US012631895B2

(12) United States Patent
Gao et al.

(10) Patent No.: US 12,631,895 B2
(45) Date of Patent: May 19, 2026

(54) ULTRAFAST LIGHT FIELD TOMOGRAPHY

(71) Applicant: THE REGENTS OF THE UNIVERSITY OF CALIFORNIA, Oakland, CA (US)

(72) Inventors: Liang Gao, Santa Clara, CA (US); Xiaohua Feng, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 702 days.

(21) Appl. No.: 18/046,016

(22) Filed: Oct. 12, 2022

(65) Prior Publication Data

US 2023/0125131 A1     Apr. 27, 2023

Related U.S. Application Data

(63) Continuation of application No. PCT/US2021/028891, filed on Apr. 23, 2021.
(Continued)

(51) Int. Cl.
*G02B 30/27* (2020.01)
*A61B 5/00* (2006.01)
(Continued)

(52) U.S. Cl.
CPC ............ *G02B 30/27* (2020.01); *A61B 5/0033* (2013.01); *G02B 21/0032* (2013.01);
(Continued)

(58) Field of Classification Search
CPC ........ G02B 27/0172; G02B 2027/0138; G02B 27/0075; G02B 2027/0127;
(Continued)

(56) References Cited

U.S. PATENT DOCUMENTS 4,238,148 A     12/1980   Courtney-Pratt
6,229,562 B1    5/2001    Kremen
(Continued)

FOREIGN PATENT DOCUMENTS

CN     1193898     9/1998
CN     1946344     4/2007
(Continued)

OTHER PUBLICATIONS

Heshmat, Barmak, et al. "Single-shot ultrafast imaging using parallax-free alignment with a tilted lenslet array." CLEO: Science and Innovations. Optica Publishing Group, 2014. (Year: 2014).*
(Continued)

*Primary Examiner* — Sumati Lefkowitz
*Assistant Examiner* — Ryan P Potts
(74) *Attorney, Agent, or Firm* — O'BANION & RITCHEY LLP; John P. O'Banion

(57) ABSTRACT

Systems and methods are provided for ultrafast light field tomography (LIFT), a transient imaging strategy that offers a temporal sequence of over 1000 and enables highly efficient light field acquisition, allowing snapshot acquisition of the complete two, three or four-dimensional space and time. The apparatus transforms targets in object space into parallel lines in the image plane with a cylindrical lens. Beam projections are optionally directed through a Dove prism and an array of cylindrical lenslets to an imaging device such as a SPAD camera, streak camera and CCD camera. By using an array of cylindrical lenslets oriented at distinct angles, enough projections are obtained simultaneously to recover the image with a single snapshot. The time-resolved system and methods were adapted to LIDAR, hyperspectral, non-line-of-sight, and three-dimensional transient imaging.

24 Claims, 7 Drawing Sheets

Related U.S. Application Data

(60) Provisional application No. 63/014,312, filed on Apr. 23, 2020.

(51) Int. Cl.

| | | |
|---|---|---|
| *G02B 21/00* | (2006.01) | |
| *G02B 27/00* | (2006.01) | |
| *H04N 13/232* | (2018.01) | |
| *H04N 23/957* | (2023.01) | |

(52) U.S. Cl.
CPC ....... *G02B 27/0075* (2013.01); *H04N 13/232* (2018.05); *H04N 23/957* (2023.01)

(58) Field of Classification Search
CPC .............. G02B 27/1066; G02B 3/0056; G02B 3/0006; G02B 30/27; G02B 30/29; G02B 6/0076; G02B 6/34; G02B 7/021; G02B 17/04; G02B 30/50; G02B 30/54; G02B 17/002; G02B 5/04; G02B 2027/0123; G02B 2027/0145; G02B 3/005; G02B 3/0037; G02B 5/045; G02B 27/0966; G02B 21/361; G02B 13/0095; G02B 21/0032; H04N 13/122; H04N 23/55; H04N 23/56; H04N 13/232; H04N 23/957; G06T 7/70; G06T 2207/10052; G06T 3/047; G06T 2207/10101; G06T 7/0004; A61B 5/0033; G06F 3/011

See application file for complete search history.

(56) References Cited

U.S. PATENT DOCUMENTS

| | | | | |
|---|---|---|---|---|
| 2007/0230944 | A1 | 10/2007 | Georgiev | |
| 2014/0263963 | A1* | 9/2014 | Broxton | G02B 27/0075 250/208.1 |

| | | | | |
|---|---|---|---|---|
| 2014/0334745 | A1 | 11/2014 | Fleischer | |
| 2016/0330432 | A1* | 11/2016 | Yu | G06T 15/205 |
| 2019/0339356 | A1* | 11/2019 | Schildknecht | G01S 7/4816 |

FOREIGN PATENT DOCUMENTS

| | | | | |
|---|---|---|---|---|
| CN | 102137618 | | 7/2011 | |
| CN | 105980810 | | 9/2016 | |
| CN | 109545640 | A * | 3/2019 | H01J 31/28 |
| CN | 110023999 | | 7/2019 | |
| WO | 2021217031 | | 10/2021 | |

OTHER PUBLICATIONS

Li, Zhengyan, et al. "Single-shot tomographic movies of evolving light-velocity objects." Nature Communications 5.1 (2014): 3085. (Year: 2014).*

Liang, Jinyang, et al. "Encrypted three-dimensional dynamic imaging using snapshot time-of-flight compressed ultrafast photography." Scientific reports 5.1 (2015): 15504. (Year: 2015).*

Liang, Jinyang, Liren Zhu, and Lihong V. Wang. "Single-shot real-time femtosecond imaging of temporal focusing." Light: Science & Applications 7.1 (2018): 42. (Year: 2018).*

Cao, Fengyan, et al. "Single-shot spatiotemporal intensity measurement of picosecond laser pulses with compressed ultrafast photography." Optics and Lasers in Engineering 116 (2019): 89-93. (Year: 2019).*

State Intellectual Property Office of the People's Republic of China, the Search Report issued Jun. 24, 2025, related Chinese application No. 202180040535X, Chinese-language document, pp. 1-10, English-language translation, pp. 11-19, claims examined, pp. 20-25.

Feng, Xiaohua et al., "Ultrafast light field tomography for snapshot transient and non-line-of-sight imaging", Nature Communications 12, 1, 2021, pp. 1-9.

ISA/US, United States Patent and Trademark Office (USPTO), International Search Report and Written Opinion issued Aug. 20, 2021, related PCT international application No. PCT/US2021/028891, pp. 1-9, with claims searched, pp. 10-15.

* cited by examiner

Point P $[x_0, y_0,, d]$
at object side

1: Pin-hole model

2: PSF convolution

3: Resampled projection

Depth-of-field arrangement

-45     -27     -12     1     -22     -37     47

Depth-sense arrangement

45     -45     15     0     -32     -20     27

40

Picosecond Laser

42 — Lens and Diffuser

44 — Lift Camera

46 — Surface

58

48 z x y

52

Reflected Light

Rotating Dove Prism Using a Rotary Stage

Cylindrical Lens: 1D Image Projection

Line Sensor: Time-of-flight Imaging

50

24 — Image Rotates with the Dove Prism

14

28 x

26

24

14

28

Perspective View

Dove Prisms with Various Rotations x

54

ULTRAFAST LIGHT FIELD TOMOGRAPHY

CROSS-REFERENCE TO RELATED APPLICATIONS

This application claims priority to, and is a 35 U.S.C. § 111(a) continuation of, PCT international application number PCT/US2021/028891 filed on Apr. 23, 2021, incorporated herein by reference in its entirety, which claims priority to, and the benefit of, U.S. provisional patent application Ser. No. 63/014,312 filed on Apr. 23, 2020, incorporated herein by reference in its entirety. Priority is claimed to each of the foregoing applications.

The above-referenced PCT international application was published as PCT International Publication No. WO 2021/217031 A1 on Oct. 28, 2021, which publication is incorporated herein by reference in its entirety.

STATEMENT REGARDING FEDERALLY SPONSORED RESEARCH OR DEVELOPMENT

This invention was made with government support under Grant Number GM128761, awarded by the National Institutes of Health and Grant Number 1652150, awarded by the National Science Foundation. The government has certain rights in the invention.

NOTICE OF MATERIAL SUBJECT TO COPYRIGHT PROTECTION

BACKGROUND

1. Technical Field

This technology pertains generally to high-speed imaging systems and methods and more particularly to light field tomography (LIFT), an imaging method that is highly efficient in recording light fields and enables snapshot acquisition of large-scale 2D time-resolved data as well as 3D and 4D imaging.

2. Background

Time-resolved imaging plays a pivotal role in a range of scientific disciplines including biology, chemistry, and physics. Despite the importance of imaging in these applications, fast acquisition of large-scale 2D time-resolved data with a picosecond resolution remains a long-standing challenge to solve. The imaging speed of current imaging devices is often limited by the limitations of technology and direct detection is not possible in many ultra-fast applications.

To date, streak cameras and intensified charge-coupled device (ICCD) sensors are parallel detectors of choice for measuring ultrafast dynamics. Although such sensors are widely used, it is necessary to perform extensive scanning either in the spatial domain (for streak cameras) or temporal dimension (for ICCDs) to obtain a 2D time-resolved data and this is an inherently time-consuming process.

A single photon avalanche diode (SPAD) is an emerging ultrafast detector with exceptional sensitivity that can achieve a temporal resolution of tens of picoseconds and has the potential for fabrication into large-format two-dimensional arrays. However, obtaining a grayscale time-resolved data still requires temporal scanning or repeated illuminations with a time correlated single photon counter (TCSPC), which leads to an inferior filling factor for 2D SPAD sensors given current fabricating technologies. The need for scanning also undesirably restricts the applicable scope of these cameras to strictly repeatable events.

The past decade has also witnessed the development of several different ultrafast cameras that are capable of 2D time-resolved imaging with a single snapshot. However, none of these methods have attained the challenging combination of a deep sequence (of over 1000) and a picosecond temporal resolution, even if active methods are considered. For instance, using specialized illumination, sequentially timed all-optical mapping photography (STAMP) can achieve a temporal resolution of 200 fs, but only a rather limited sequence depth (<50) is obtainable. On the other extreme, serial time-encoded amplified imaging (STEAM) can stream 2D images continuously while its temporal resolution is restricted to a few nanoseconds.

Compressive ultrafast photography (CUP) has been the only passive camera that offers a three-dimensional data cube (x, y, t) over 100×100×100 in a single snapshot and reached a sub-picosecond resolution. Unfortunately, it is challenging to scale it further for larger scale measurements, apart from its inherent tradeoff between the spatial resolution and sequence depth, the large compression factor and spatial-temporal cross talk of a CUP camera directly limits the achievable spatiotemporal resolution in transient imaging.

Nevertheless, existing ultrafast cameras fall short for non-line-of sight imaging, which requires a high-resolution, two-dimensional ultrafast camera that offers a long sequence of time-resolved data. Current non-line-of-sight implementations, therefore, need to perform scanning in spatial and/or temporal dimensions, which elongates the acquisition time to the level of seconds or longer, restricting the approach to imaging static or slowly moving objects even when the image resolution is compromised.

The lack of a general tool for single-shot acquisition of large-scale 2D time-resolved data and the inability to cope with extended 3D scenes not only restrict the visualization of transient phenomena in direct view, but also compromises the capability of seeing around occlusions or, non-line-of-sight (NLOS) imaging. While looking beyond direct view finds broad applications in domains like navigation, surveillance, and even medical imaging, current NLOS imagers still lag far behind their line-of-sight counterparts in achieving video-rate imaging, though recent work has opened the pathway of systematically transferring line-of-sight imaging methods to the NLOS domain. The major bottleneck with the computationally intensive reconstruction being lifted off by faster inversion algorithms and parallel computing remains the slow acquisition of large-scale time-resolved data. Although edge-resolved transient imaging (ERTI) uses far fewer scans for NLOS imaging, it only yields a 2.5D (rather than a full 3D) reconstruction, and its differential measurement still leads to a long exposure time (>10 s) at each scanning position. Faster scanning can also be achieved in several other ways including shortening the sensor exposure time, reducing the spatial scanning density, or parallelizing the acquisition. Nevertheless, the scanning mechanism deficiencies persist, and the resultant smaller photon counts from shorter exposure typically need to be compensated by using a higher laser power and/or retro-reflective targets. The inability to cope with extended 3D scenes also precludes field-deployable NLOS imaging, which needs to accommodate non-planar or even disconnected surfaces. These obstacles make NLOS imaging arguably one of the most challenging applications for ultrafast cameras.

BRIEF SUMMARY

Systems and methods are provided for ultrafast light field tomography (LIFT) that addresses the deficiencies in conventional non-line-of-sight imaging and enables many important adaptations. Existing ultrafast cameras are incapable of coping with extended three-dimensional scenes and fall short for non-line-of-sight imaging that requires a long sequence of time-resolved two-dimensional data. Therefore, current non-line-of-sight imagers need to perform extensive scanning in the spatial and/or temporal dimensions, which restricts their use to imaging only static or slowly moving objects.

The present technology addresses these long-standing challenges with a transient imaging strategy called ultrafast light field tomography. Light field tomography provides devices and imaging methods that are very efficient in recording light fields and enables snapshot acquisition of large-scale 2D time-resolved data. This is achieved by transforming a one-dimensional 1D sensor to a 2D light field camera, exploiting the fact that conventional light field acquisition is highly redundant since the sub-aperture images are mostly the same except for disparity cues. The vastly faster frame rate of 1D sensors also benefits LIFT for high-speed imaging. While prior state-of-the-art ultrafast cameras are severely limited in pixel resolution that prevents light field acquisition, LIFT provides a way to break this restriction. Coupled with a streak camera, LIFT can capture the complete four-dimensional spatiotemporal space in a single snapshot and may provide an image resolution of over 120×120 with a sequence depth beyond 1000, enabling unprecedented ultrafast imaging capabilities, including video-rate NLOS imaging using a low powered laser.

The illustrated LIFT methods offer a temporal sequence of over 1000 and enables highly efficient light field acquisition, allowing snapshot acquisition of the complete four-dimensional space and time. With LIFT processes, three-dimensional imaging of light in flight phenomena with a <10 picoseconds resolution and non-line-of-sight imaging at a 30 Hz video-rate has been demonstrated. Furthermore, the LIFT processing can benefit from deep learning techniques for an improved and accelerated image formation. LIFT may also facilitate broad adoption of time-resolved methods in various disciplines.

The typical LIFT system provides a streak camera or other instrument for measuring light intensity variations in a light pulse over time and a cylindrical lens, dove prism array, cylindrical lenslet array, optional slit array and imaging optics and imaging sensor. The cylindrical lenslet array is closely secured to the entrance slit of the streak camera. With this configuration, three-point sources in the object space can be transformed into parallel lines on the image plane, producing a projection image. Acquiring such projection images from different perspectives using lenslets that are oriented at different angles, naturally samples the light field of the 3D scene. The 1D projection data is obtained by sampling the convolution result of the pinhole image and line-shaped point spread function (PSF). Recording such 1D data over time will yield a time-resolved measurement. A lenslet is literally a small lens. The fact that distinguishes it from a small lens is that it is part of a lenslet array.

The core idea of LIFT is to reformulate photography as a computed tomography (CT) problem by using cylindrical lenses to acquire en-face parallel beam projections of the object. Generally, the preferred implementation of light field tomography begins with the transformation of point sources in the object space into parallel lines in the image plane by a cylindrical lens. The line direction in the image space is parallel to the invariant axis (i.e. the axis without optical power) of the cylindrical lens.

Such an optical transformation of a scene can be artificially decomposed into two steps. The first step is pin-hole image formation, and the second step is convolution with a line-shaped point spread function that is parallel with the invariant axis of the cylindrical lens. The line-shaped PSF allows an individual camera pixel to integrate the image along that line. With a 1D sensor positioned at the center of the image space, a parallel beam projection of the image is acquired along the invariant axis direction.

Projections at different angles can be recorded by rotating a cylindrical lenslet with respect to the 1D sensor. By using an array of cylindrical lenslets oriented at distinct angles, one can obtain enough projections simultaneously to recover the image with a single snapshot. Furthermore, because each lenslet observes the same scene from different perspectives, the light field of the scene is naturally sampled in the projection data with an angular resolution equal to the number of lenslets. Such tomographic light field recording is orders of magnitude more efficient than conventional approaches. This endows LIFT with full-fledged light field imaging capabilities, including depth retrieval, post-capture refocusing, and extended depth of field.

For example, LIFT also permits the fabrication of 2D camera arrays with 1D sensors for ultrafast or synthetic-aperture imaging, featuring an orders of magnitude smaller data load than conventional approaches. The larger baseline and etendue in camera arrays will also enable vastly larger light throughput, making it possible to see through occlusions.

Given its unique snapshot acquisition of a large-scale time-resolved light field data, LIFT may also find a broad range of applications that are previously hindered by prolonged time-domain measurements, such as imaging into or through scattering medium via time domain diffuse optical tomography. The methods can also be readily extended to an optical dimension other than time, such as spectral domain by using an imaging spectrometer as the 1D sensor and thereby enabling snapshot light field hyperspectral imaging. With spectral encoding being the foundation of active ultrafast cameras, spectral domain LIFT may turn an off-the-shelf imaging spectrometer into an ultrafast camera with sub-100 fs temporal resolution and a sequence depth over 1000, provided that an appropriate illumination is available. For example, the functionality of the LIFT system and processing methods is illustrated with applications such as hyperspectral imaging, Light Detection and Ranging (Lidar) and Non-line-of sight (NLOS) imaging.

According to one aspect of the technology, an apparatus and system are provided for performing ultrafast light field tomography that exhibits exceptional resolution even when objects are in rapid motion and out of the field of focus.

A further aspect of the technology is to provide stable light field imaging platform that incorporates deep learning strategies that improves image quality and substantially accelerates image formation.

Another aspect of the technology is to provide an apparatus and system that enables video-quality, NLOS imaging by capturing the complete four-dimensional space (x,y,z, and time) in a single snapshot.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, systems and methods for ultrafast light field tomography are generally shown. Several embodiments of the technology are described generally in FIG. 1 to FIG. 8 to illustrate the characteristics and functionality of the devices, systems, and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
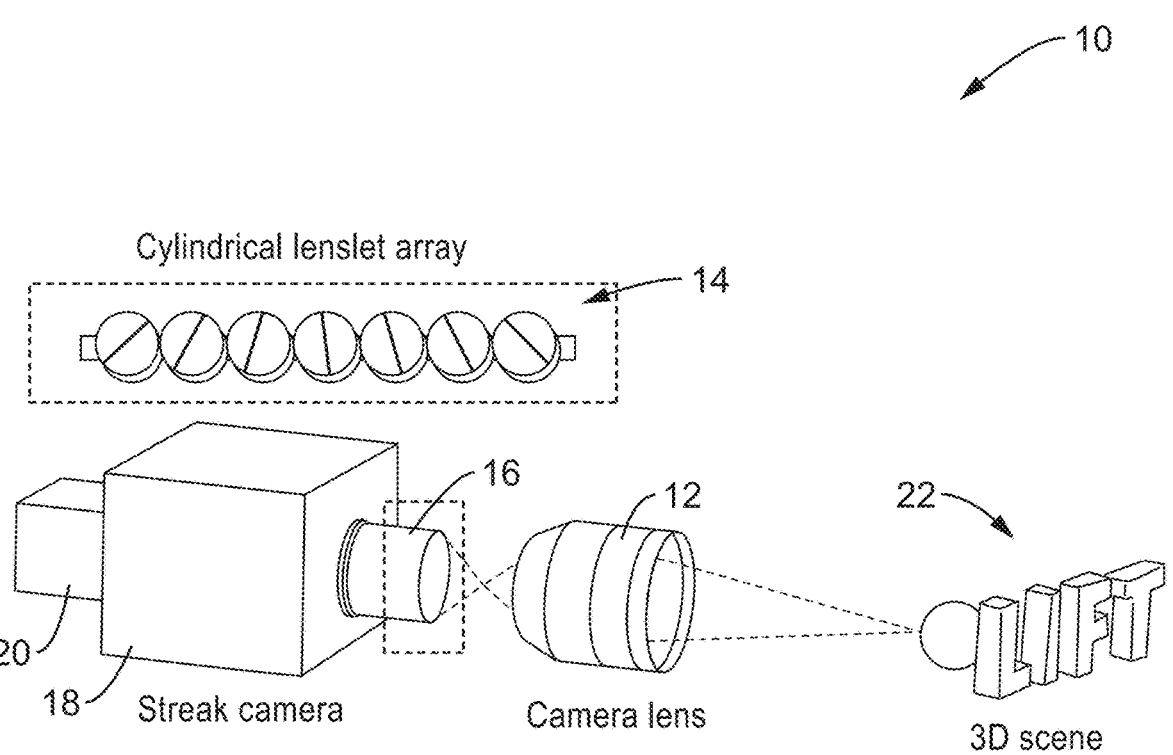
FIG. 1 is a schematic representation of the LIFT camera with relay lens, cylindrical lenslet array and streak camera according to one implementation of the technology. The cylindrical lenslet array is closely secured to the entrance slit of the streak camera in this illustration.

Turning now to FIG. 1, one embodiment of the LIFT camera 10 for performing light field tomography is shown schematically. Here, the ultrafast LIFT system is configured with a camera lens 12 and an array of cylindrical lenslets 14. In this embodiment, several cylindrical lenslets (e.g. 2 mm diameter-focal length 8 mm) that are oriented at distinct angles are assembled in a holder and aligned with the entrance slit 16 of a streak camera 18. The array of cylindrical lenslets 14 is preferably closely secured to the entrance slit 16 of the streak camera 18. The lenslet arrangement (the sequence of the invariant axis' angles with respect to the slit) can be flexibly adjusted to be optimized for different applications, such as a built-in extended depth of field.

The 3D scene 22 is imaged by the camera 12 lens to the intermediate image space, from which the cylindrical lenslet 14 array forms differently projected sub-images onto the slit plane. A field stop may be placed in the intermediate image plane to reduce the field of view to avoid potential sub-image overlap between the adjacent lenslets 14.

The streak camera 18 relays the 1D projection images extracted by the entrance slit 16 onto a photocathode, converts it to the electronic domain, and eventually deflects it onto different rows of a CCD camera 20 according to the time of arrival of the photons. Because the temporal axis is orthogonal to the 1D projection image, there is no spatial-temporal coupling in LIFT, leading to an optimal temporal resolution.

The LIFT imaging methods bridge the gap of snapshot acquisition of large-scale 2D time-resolved measurement and breaks the data bandwidth limit of conventional cameras. This is achieved by transforming any one-dimensional (1D) sensors to (2D) light field cameras, exploiting the fact that fast cameras are mostly in a 1D format. Coupled with a streak camera 18, LIFT can capture the complete four-dimensional spatiotemporal space in a single snapshot and provide an image resolution over 120×120 with a sequence depth beyond 1000, enabling unprecedented ultrafast imaging capabilities, including video-rate NLOS imaging, Light Detection and Ranging (Lidar) and Hyperspectral LIFT imaging.

Figure 2A:
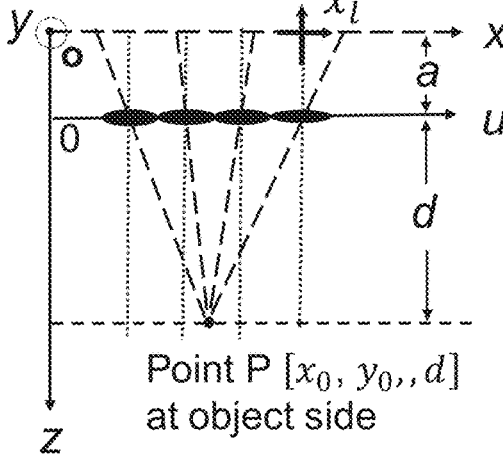
FIG. 2A is a graph of the two-plane parameterization of the light field of the image acquisition.
Figure 2B:
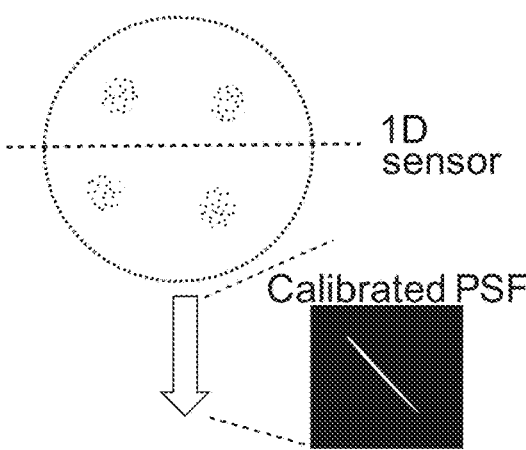
FIG. 2B depicts image formation of LIFT modelled by a three-step decomposition of the acquisition shown in the embodiment of FIG. 2A.
Figure 2B:
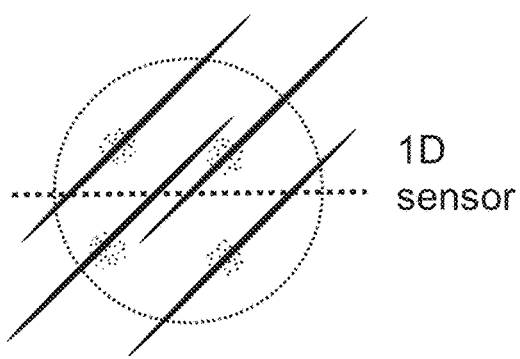
Figure 2B:
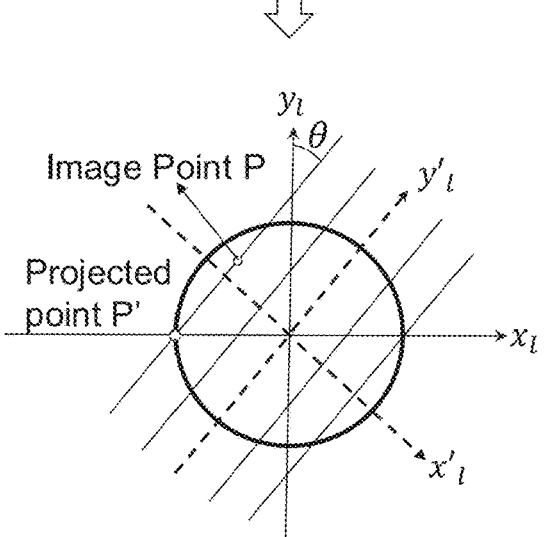

The two-plane parameterization of light and image formation modelling of LIFT are illustrated in FIG. 2A and FIG. 2B. By using an array of cylindrical lenslets oriented at distinct angles, enough projections can be obtained simultaneously to recover the image with a single snapshot. For clarity, only four lenslets are shown in FIG. 2A, where the spatial axis (x) coincides with the sensor plane, and the angular axis (u) resides on the lenslet-array plane. Each lenslet is also assigned with a local coordinate $x_l$, whose origin is the image of a point source located at infinity (indicated by the dashed parallel lines).

The image formation onto a 1D sensor by a cylindrical lenslet is artificially decomposed into three steps here: (1) pin-hole image formation, (2) PSF substitution, and (3) resampled projection as shown in FIG. 2B.

Step 1: Pin-Hole Image Formation Model

This is the classical imaging process. Consider a point source located at $[x_0, y_0, d]$, the pin-hole model predicts its local coordinates on a sub-image as:

$$\begin{cases} x_l = \dfrac{a}{d}(u - x_0) & (a) \\ y_l = -\dfrac{a}{d}y_0 & (b) \end{cases} \tag{1}$$

Step 2: PSF Convolution

A cylindrical lenslet differs from a perfect spherical lens in lacking optical power along one axis, which is referred to as the invariant axis. For a point source, it forms a finite line along the invariant axis at the image plane. The line length is determined by the image magnification $m=d/a$ of the system and the lenslet size as $l=(1+1/m)q$, where q is the lenslet diameter. Such a line-shaped PSF disperses each point in the image space onto a pixel on a 1D sensor, as illustrated by the transition from Step 1 to Step 2 in FIG. 2B. Therefore, an individual pixel integrates the image along the PSF-line, and a parallel beam projection of the image is obtained on the 1D sensor along the angle of the invariant axis.

Step 3: Resampled Projection

For a fixed 1D sensor, the projection along different angles is acquired by rotating the cylindrical lenslet. As a result, the 1D sensor is generally not perpendicular to the projection direction. This is illustrated in Step 3 of FIG. 2B, where solid black lines indicate the projection direction and the $x_1$ axis represents the 1D sensor. To relate the unknown image to the acquired projection data via Fourier slice theorem, it is necessary to make the projection perpendicular to the 1D sensor. This can be done by a computational resampling process. Denoting the angle between the projection and the $y_l$ axis as $\theta$, one can establish a local coordinate $[x_l', y_l']$, shown in dashed lines, to obtain a virtual sensor line $x_l'$ that is perpendicular to the projection direction. These two local coordinates are related by a rotation matrix:

$$\begin{bmatrix} x' \\ y' \end{bmatrix} = R_\theta \begin{bmatrix} x \\ y \end{bmatrix} = \begin{bmatrix} \cos\theta & -\sin\theta \\ \sin\theta & \cos\theta \end{bmatrix} \begin{bmatrix} x \\ y \end{bmatrix}. \tag{2}$$

Combining Eq. (1) and (2), the image point in the auxiliary coordinate system is obtained as:

$$\begin{cases} x_l' = \dfrac{1}{m}(u - x_0)\cos\theta - \dfrac{1}{m}y_0\sin\theta & (a) \\ y_l' = \dfrac{1}{m}y_0\sin\theta + \dfrac{1}{m}y_0\cos\theta & (b) \end{cases} \tag{3}$$

The projection onto the virtual line sensor is done by simply dropping the y component:

$$\begin{cases} x_l' = \dfrac{1}{m}[-x_0 - y_0\tan\theta + u]\cos\theta & (a) \\ y_l' = 0 & (b) \end{cases} \tag{4}$$

Substituting the result back into Eq. (2), the experimentally recorded projection data is obtained as $x_l = x'_l/\cos\theta$. The $\cos\theta$ term is designated as the resampling factor as it resamples the experimentally recorded projection data (on the sensor line $x_l$) onto the desired recording line $x'_l$. In other words, each cylindrical lenslet performs a resampled projection onto the 1D sensor $x_l$. Ultimately, the LIFT imaging acquisition can be summarized into a single equation:

$$x_l' = \frac{1}{m}[-x_0 - y_0\tan\theta + u]\cos\theta. \tag{5}$$

The first two terms of the equation describe the projection process, and the third term is the light field component contributed by different lenslets, which enables post-capture refocusing and depth retrieval.

The Fourier transform of the resampled projection is a slice of the two-dimension Fourier transform (k-space) of the original image. For image reconstruction, therefore, it is necessary to fill the complete k-space by acquiring projection data at a sufficient number of angles spanning the range of $[0°, 180°]$. A general rule for this criterion states that to reconstruct an N×N image, N projections with ~N pixels resolution is needed. Using 1D sensors with a limited pixel count (several thousands) for an image resolution over 100×100, one practical implementation of LIFT usually restricts the number of projections on the order of ten. This casts LIFT as a sparse view CT problem. Using n lenslets, the compression factor in LIFT for sampling an N×N image is therefore N/n, which is on the order of ten for most implementations. To minimize the correlations in the projection data in LIFT and therefore maximize information content for reconstruction, it is also beneficial to arrange the projection angle uniformly.

With a 1D sensor being fixed, the practical angular range of the projection is also limited by only rotating the cylindrical lenslet. The maximum height for a point detectable by the 1D sensor will be limited to $h=l\cos\theta/2$. This implies the achievable field of view is $2 h=l\cos\theta$. As a result, one must strike a balance between the FOV and angular range. In practical implementations, the angular range is limited to $[\theta_1, \theta_2]$, leading to a missing cone in the k-space. Tomographic reconstruction in this case results in degraded image quality, which is referred to as the limited view problem. The LIFT implementation may suffer from a limited view problem since the angular range of projection is about $[-45°, 45°]$ with respect to the y axis. There are several methods for mitigating the limited view problem.

One method is mathematical, using deep learning to train a neural network for the system with enough data that is afflicted by the limited view problem so the network can learn the pattern (or statistical distribution) of imperfections in the reconstructed image and correct the image thereafter. This solution is system-specific and can substantially mitigate, but not eliminate, the limited view problem.

Figures 5A, 5B:
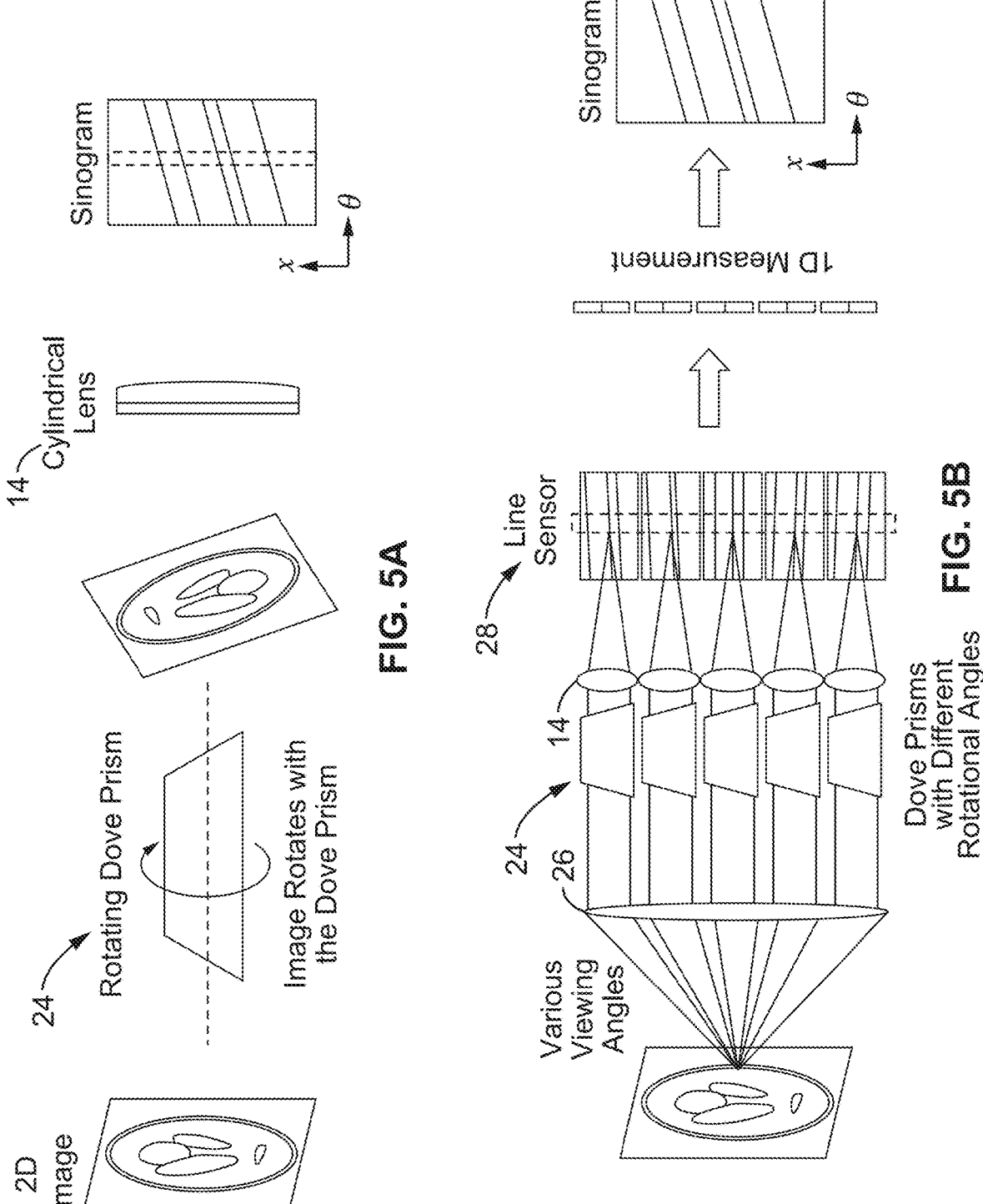
FIG. 5A is a schematic side view of a LIFT camera using a single image rotating dove prism according to one embodiment of the technology.
FIG. 5B is a schematic side view of a LIFT camera using an array of image rotating dove prisms according to one implementation of the technology.

The second method is to insert a Dove prism after a relay lens and before the cylindrical lenses, which projects the image of the original object to infinity as shown in FIG. 5A. The Dove prism may be rotated by 45 degrees so that the image passing through it is rotated by 90 degrees, allowing the cylindrical lenslet behind it to fill in the missing cone and thus eliminating the limited view problem. The downside of using a Dove prism is that it can introduce an astigmatism for non-collimated light and chromatic aberrations for broadband scenes, compromising the 3D imaging performance of LIFT.

Another practical method is to rotate the camera or equivalently, build a camera array. This requires the camera to be compact when using rotation and the intended applications need to be repeatable such as with NLOS imaging using compact SPAD cameras. For example, rotating a LIFT camera with 7 lenslets by 3 times will not only enrich the projections to 21 for eliminating the limited view problem and will also extend the light field to 2D. A similar gain can be obtained by a camera array implementation. Because the deep learning method has the advantage of simplicity and faster image reconstruction, it is the preferred method.

Figure 3:
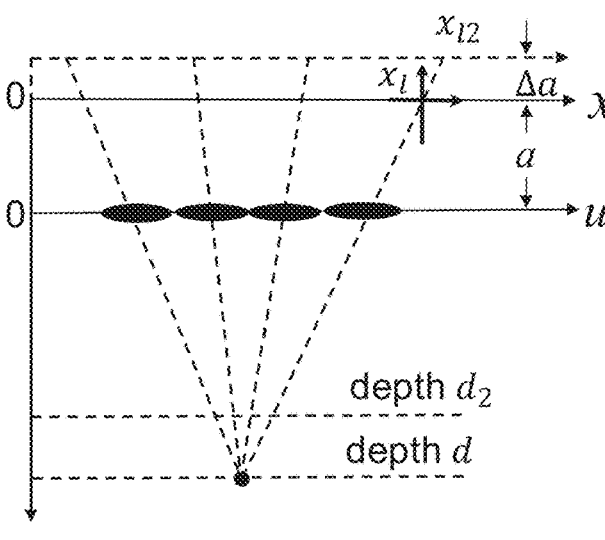
FIG. 3 is a graph of the two-plane parameterization of the light field propagation through different planes for refocusing according to one implementation of the technology.

The LIFT light field imaging system also permits post-capture refocusing. As depicted in FIG. 3, to focus on a different plane $d_2$, the 1D sensor needs to be moved by $\Delta\alpha$. The light field at the new virtual sensor plane is calculated as:

$$x_{l2} = \left(1 + \frac{\Delta a}{a}\right)x_l - \frac{\Delta a}{a}u = \left(1 + \frac{\Delta a}{a}\right)[x_l + su], \tag{6}$$

where $s=-\Delta\alpha/(\Delta\alpha+\alpha)$. Ignoring the magnification factor $$\left(1 + \frac{\Delta a}{a}\right),$$

which is constant across the whole image area when computationally refocusing, one can rewrite Eq. (6) as:

$$x_{l2}=x_l+su. \tag{7}$$

This is the same refocusing formula in the ray space for light field cameras except that LIFT captures only the angular information along one axis (u) instead of two. Hence, refocusing onto different depths can be achieved in LIFT by shearing-and-reconstructing: shear the acquired projection data and then perform image reconstruction. This is also clear from Eq. (5), which describes the light field at plane d when the nominal focal plane is at infinity.

It is also possible to computationally extend the depth of field in LIFT. In one embodiment, the measurement data is processed to reconstruct an image set computationally refocused on all different depths. Next, the sharpest feature around a region of interest (ROI) for each pixel is identified across the image set, and an all-in-focus image is subsequently assembled by combining the sharpest parts via graph cut algorithms. Such an extended depth of field is obtained at the expense of processing time, however, and requires the image to show enough features. The depth-of-field version of LIFT described herein sidesteps these two drawbacks altogether.

The LIFT system can achieve an extended depth of field without resorting to computational refocusing by the judicious arrangement of the cylindrical lenslets so that an all-in-focus image can be automatically obtained. By adding a shearing term to Eq. (5) for refocusing, the following is obtained:

$$\frac{x_l'}{\cos\theta} = -\frac{1}{m}[x_0 + y_0\tan\theta - u] + su = -\frac{1}{m}[x_0 - u] - \frac{1}{m}[y_0\tan\theta - msu] = \tag{8}$$

$$-\frac{1}{m}[x_0 - u] - \frac{1}{m}\left[y_0 - \frac{m}{\tan\theta}su\right]\tan\theta = -\frac{1}{m}[x_0 - u] - \frac{1}{m}[y_0 - \Delta y]\tan\theta$$

$$\frac{x_l'}{\cos\theta} = -\frac{1}{m}[x_0 + y_0\tan\theta - u] + su = -\frac{1}{m}[x_0 - u] - \frac{1}{m}[y_0\tan\theta - msu] =$$

$$-\frac{1}{m}[x_0 - u] - \frac{1}{m}\left[y_0 - \frac{m}{\tan\theta}su\right]\tan\theta = -\frac{1}{m}[x_0 - u] - \frac{1}{m}[y_0 - \Delta y]\tan\theta,$$

$$\frac{x_l'}{\cos\theta} = -\frac{1}{m}[x_0 + y_0\tan\theta - u] + su = -\frac{1}{m}[x_0 - u] - \frac{1}{m}[y_0\tan\theta - msu] =$$

Figure 4A:
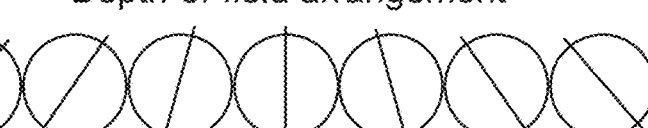
FIG. 4A is a cylindrical lenslet array with the lenslet arrangement configured for the depth-of-field version of LIFT, with black solid line representing the invariant axis of the cylindrical lenslet numbered angles of the y axis (counterclockwise being the positive direction).

-continued $$-\frac{1}{m}[x_0 - u] - \frac{1}{m}\left[y_0 - \frac{m}{\tan\theta}su\right]\tan\theta = -\frac{1}{m}[x_0 - u] - \frac{1}{m}[y_0 - \Delta y]\tan\theta$$

$$\frac{x_l'}{\cos\theta} = -\frac{1}{m}[x_0 + y_0\tan\theta - u] + su = -\frac{1}{m}[x_0 - u] - \frac{1}{m}[y_0\tan\theta - msu] =$$

$$-\frac{1}{m}[x_0 - u] - \frac{1}{m}\left[y_0 - \frac{m}{\tan\theta}su\right]\tan\theta = -\frac{1}{m}[x_0 - u] - \frac{1}{m}[y_0 - \Delta y]\tan\theta$$

where $$\Delta y = \frac{m}{\tan\theta}$$

su is the shift in the object space due to refocusing. Notably, there is an interaction between the lenslet projection angle $\theta$ and the angular component u of the light field. If the cylindrical lenslets are arranged in such a manner that the angle $\theta$ as a function of the angular u axis satisfying:

$$\tan\theta \approx ku, \tag{9}$$

then $$\Delta y = \frac{m}{k}s$$

will be a constant that is independent of the angular variable u, meaning no blurring in the resultant image because all lenslets contribute the same shift for a specific object plane (indexed by s). The object plane at different depths is indeed shifted from the nominal center by an amount determined by its defocus distance, but each plane is well focused. This makes the reconstructed image automatically all-in-focus. An example of the configuration is shown in FIG. 4A as the depth-of-field arrangement. Furthermore, it is feasible to undo this automatic all-in-focus imaging effect and computationally defocus by changing the shearing term s from a constant to a lenslet-specific number s×tan $\theta$. The cost of this arrangement is a degraded depth retrieval accuracy because only residual defocus errors are left, which are contributed by the approximation error in Eq. (9).

To optimize lenslet configuration for 3D imaging, the tan $\theta$ value may be expanded as a function of the variable u into a Taylor series:

$$\tan\theta = f(u) = m_1 u + m_2 u^2 + \tag{10}$$

Figure 4B:
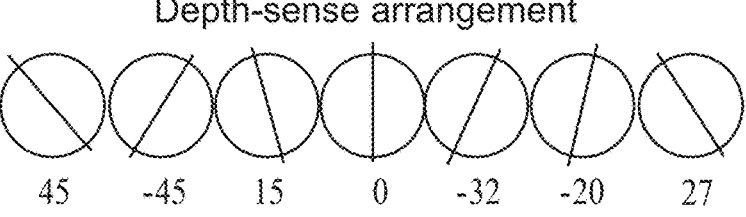
FIG. 4B is a cylindrical lenslet array with the lenslet arrangement configured for the depth-sense version of LIFT, with black solid line representing the invariant axis of the cylindrical lenslet and numbered angles of the y axis (counterclockwise being the positive direction).

Substituting into $\Delta y$, it becomes evident that maximizing the first-order coefficient $m_1$ leads to the depth-of-field lenslet configuration, whereas minimizing it to zero will maximize the defocus error and hence optimize depth retrieval. It is straightforward to perform a search over the permutations of a pre-determined set of projection angles to find the near-optimum configuration for depth retrieval. The resultant configuration is shown in FIG. 4B and identified as the depth-sense arrangement. The lenslet arrangements for the depth-of-field and depth-sense versions of LIFT shown in FIG. 4A and FIG. 4B as black solid lines representing the invariant axis of the particular cylindrical lenslet. The angles noted underneath each lenslet are the w.r.t and the y axis (counterclockwise being the positive direction) and listed with an accuracy of 1 degree for clarity.

The image rotation in LIFT can also be achieved through a Dove prism as shown in the embodiments shown in FIG. 5A and FIG. 5B. The dove prism is an optical element that can rotate an input image. FIG. 5A is a schematic illustration of a LIFT implementation using a single rotating Dove prism 24. A cylindrical lens 14 is used after the Dove prism 24 to focus the image into lines. A one-dimensional detector array (i.e., a line image sensor) 28 measures the transformed image. By rotating the Dove prism 24 and capturing the corresponding line image at varied angles, it is possible to construct a sinogram. The vertical axis is the spatial axis along the 1D detector array direction, and the horizontal axis is the angle. A 2D image can then be computed by applying any standard computed-tomography (CT) reconstruction algorithm to the sinogram that is obtained.

The LIFT methods can also be implemented using an array of Dove prisms 24 as shown in FIG. 5B. A single objective lens 26 images a 3D object. At the back pupil plane of the objective lens 26 is placed an array of the dove prisms 24, followed by an array of cylindrical lenses 14. The rotation angles of the dove prisms 24 vary on the array, covering the range of 0-180°. The Dove prism array can be arranged either in a 1D or 2D format. For example, FIG. 5B shows a 1D format Dove prism array configuration. The cylindrical lenses focus the rotated images into line images. At the detector plane, to measure the transformed images, either a 1D detector array (for 1D Dove prism array configuration) or multiple spaced 1D detector arrays (for 2D Dove prism array configuration) are used. Next, the constructed sinogram allows the reconstruction of the image. Because the projection images are acquired at varied angles, the depth can be derived based on the disparity among different view images. The numerical refocusing, extended depth of field, and 3D rendering can also be enabled by standard light field image processing.

The LIFT light field imaging system also permits the extraction of depths using a depth-from-focus (DfF) method, thereby yielding a 3D image at each time instance. In DfF, the camera captures a sequence of images of the scene at different focal settings, producing a focal stack. To infer depth, a focus measure (sum of modified Laplacian) is computed for each pixel of the image, and the focal setting giving rise to the maximum focus measure is identified, which can be mapped to a depth value. For light field cameras like LIFT, the focal stack is captured with a single snapshot and produced computationally by refocusing the image at different depths.

Figure 6:
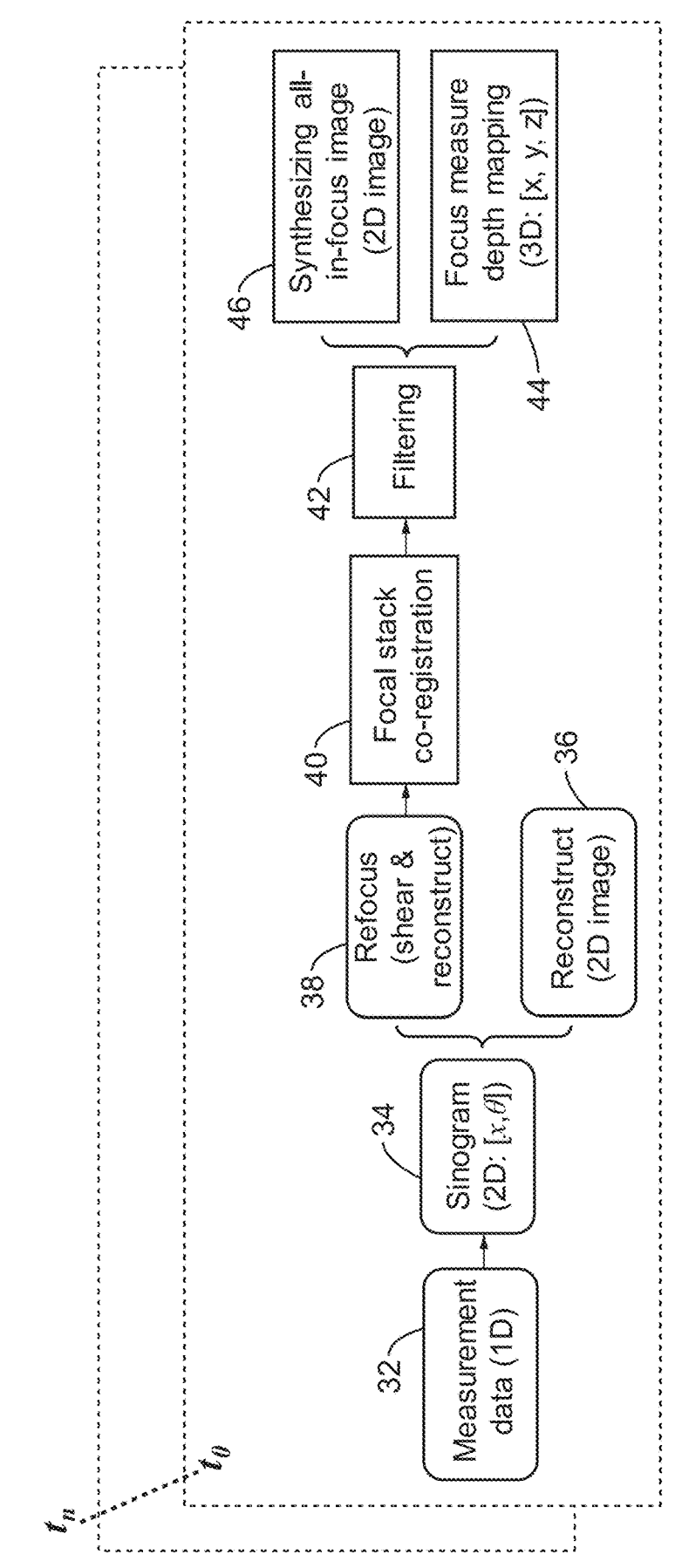
FIG. 6 is a functional block diagram of a method for processing 2D (x, y) and 3D (x, y, z) imaging in LIFT. For 4D (x, y, z, t) imaging, the 3D image processing is individually applied at each time instance according to one embodiment of the technology.

The processing pipeline 30 of LIFT for reconstructing multi-dimensional images (2D, 3D, and 4D) is summarized in the block diagram of FIG. 6. At block 31 of FIG. 6, 1D measurement data is acquired from the imaging apparatus as illustrated above. Each 1D measurement data obtained at block 31 is ordered into a sinogram (the projection data (x, θ)) at block 32. This ordered data can be directly reconstructed into a 2D (x, y) image at block 33 or it can go through a shear-and-reconstruction process to refocus on different depths at block 34 to produce a focal stack.

Thereafter, the focal stack may be co-registered at block 35 because the refocusing can induce image shifts. In one embodiment, the denoising algorithm VBM3D is then applied to attenuate the refocusing artefacts in the focal stack, which substantially improves the robustness of depth retrieval at block 36. Other filtering may also be applied at block 36. Finally, the focus measure is computed for each pixel, and a quick sorting algorithm may be used to identify the correct focal setting and map that pixel to the corresponding depth, yielding the 3D image (x, y, z) at block 37. As a result of the decoupled space-time acquisition in LIFT, the 2D and 3D image processing are independently performed at each time instance to produce the final 3D (x, y, t) or 4D (x, y, z, t) results. An all-in-focus 2D image may also be synthesized at block 38. The figure also indicates using a deep adjoint neural network (DANN) 39, as described below.

A relay system with a magnification of M changes the depth retrieval accuracy by $M^2$. For a plane at [0, 0, d], the distance between the leftmost and rightmost sub-images is:

$$L = \frac{d+a}{d}D, \tag{11}$$

where D is the baseline length of the lenslet array and a is its distance to the sensor. To connect depth d with refocusing parameter s, it is noted that the distance L at infinity is $L_\infty=D$ and refocusing from infinity onto depth d involves shearing the light field, which leads to $L_\infty=L+s(u_l-u_r)=L+sD$, where $u_l$ and $u_r$ indicates the leftmost and rightmost angular components, respectively. Solving above equation yields $$d = \frac{a}{s}.$$

The depth retrieval accuracy $\Delta d$ is the minimum depth change that causes a one-pixel variation in the distance L. Given a linear sensor with $N_x$ pixels across the baseline, a one-pixel change is $\Delta L=D/N_x$. Taking the derivative of Eq. (11) with respect to d, one obtains $$\Delta d = \frac{d^2}{Da}\Delta L = \frac{d^2}{N_x a} = \frac{m^2 a}{N_x}.$$

As α equals approximately to the lenslet focal length f, the depth retrieval accuracy can be estimated as $$\Delta d = \frac{m^2 f}{N_x}.$$

In practical system implementations, there may be some misalignments between the 1D sensor and the individual cylindrical lenslets, which will affect image quality if they are not accounted for. As the misalignment of a lenslet shifts the image from its ideal position by a vector $\vec{r}$, it can be modeled as a convolution operation with a shifted Dirac delta function $\delta(x-\vec{r})$. The forward model in LIFT can then incorporate the non-ideal effect as:

$$y=ABx=Ax', \tag{12}$$

where x' is the uncorrected image vector, and B is the convolutional matrix:

$$B = \begin{bmatrix} P_1 \\ P_2 \\ \vdots \\ P_n \end{bmatrix}, \tag{13}$$

with $P_i$ being the block Toeplitz matrix of point spread function of lenslet i. By calibrating with an arbitrary point source, indicated as vector $e_k$, one can reconstruct the point spread function of the non-ideal system as $x'=PSF'=Be_k$, which recovers the matrix B. The true image x can then be recovered by deconvolving x' with the calibrated PSF' using the Richard-Lucy algorithm.

The image quality of LIFT also depends on both the compression factor, or equivalently, the number of projections, and the signal to noise ratio of the measurement data. As shown above, a larger number of projections will fill the k-space more densely and therefore lead to better reconstruction quality in LIFT due to the reduced compression factor.

In summary, the light field data acquisition of LIFT can be encapsulated into a single equation: ignoring image magnification, the projected coordinate of a point source located at $(x_0, y_0)$ is $x_i = -x_0 - y_0 \tan \theta + u$ on the 1D sensor, where u denotes the angular component contributed by the lenslet array and $\theta$ is the orientation angle of the lenslet. The acquired projection data in LIFT relates to the en-face object via the Fourier slice theorem after computational resampling. The imaging process can be written as b=Ag, where b is the measurement data, g is the vectorized two-dimensional (2D) image, and A is the forward operator representing the parallel-beam projections at different angles. The underlying image can be recovered by inverting the above equation with a range of methods such as the analytic filtered back projection. Typically, the selection of the number of lenslets that are used may be dictated by the Nyquist sampling criterion for high-quality image reconstruction. This is generally impractical for high-resolution 2D imaging due to the limited pixel number of 1D sensors. However, under the framework of compressive sensing, the number of projections required for image reconstruction can be substantially reduced.

Since dimensional data tends to be highly compressible, the spatial image (x, y) at each time instance of the spatiotemporal datacube (x, y, t) is far simpler than natural photographs and consequently the data can be efficiently encoded in certain representation bases. Particularly for NLOS imaging, the instantaneous image on the wall can be represented with only approximately tens of projections for high quality reconstruction of complex hidden scenes. This particular embodiment renders LIFT similar to sparse view CT, which generally requires slower iterative methods for reconstruction and is prone to degraded image quality in certain scenarios.

To mitigate these two issues, a deep adjoint neural network (DANN) was devised to accelerate and improve LIFT image recovery, which incorporates the adjoint operator $A^T$ of the system into a deep convolutional neural network and thereby avoids the blind end-to-end training typical in previous endeavors. This facilitates the deep neural network to generalize well even when it is trained on a small data set. The synergy between compressive data acquisition and fast deep neural network reconstruction breaks the data bandwidth limit of conventional cameras and enables high-resolution 2D imaging with 1D sensors.

Figure 7A:
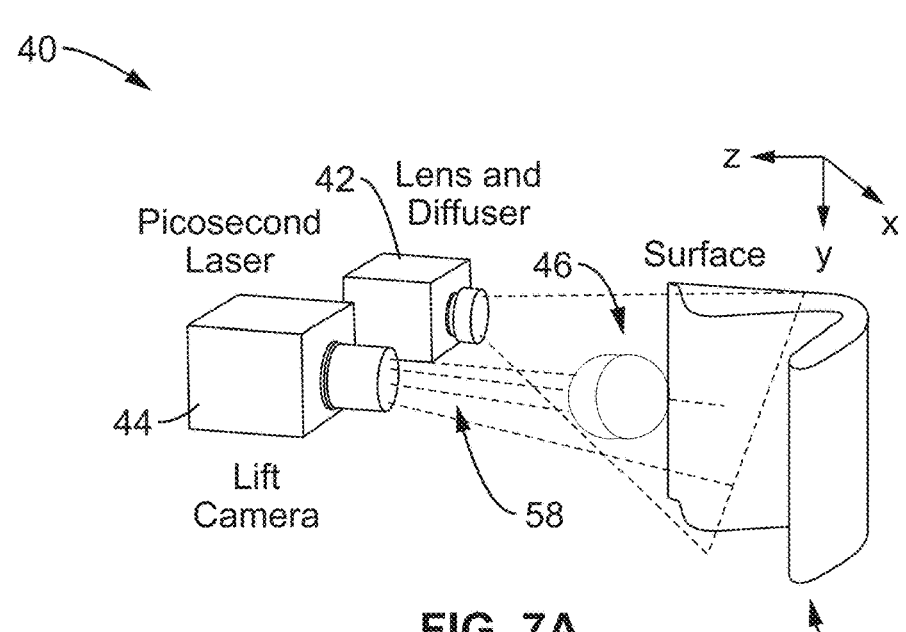
FIG. 7A is a schematic representation of the LIFT camera with associated laser with lens and diffuser system configuration for LIDAR.
Figure 7B:
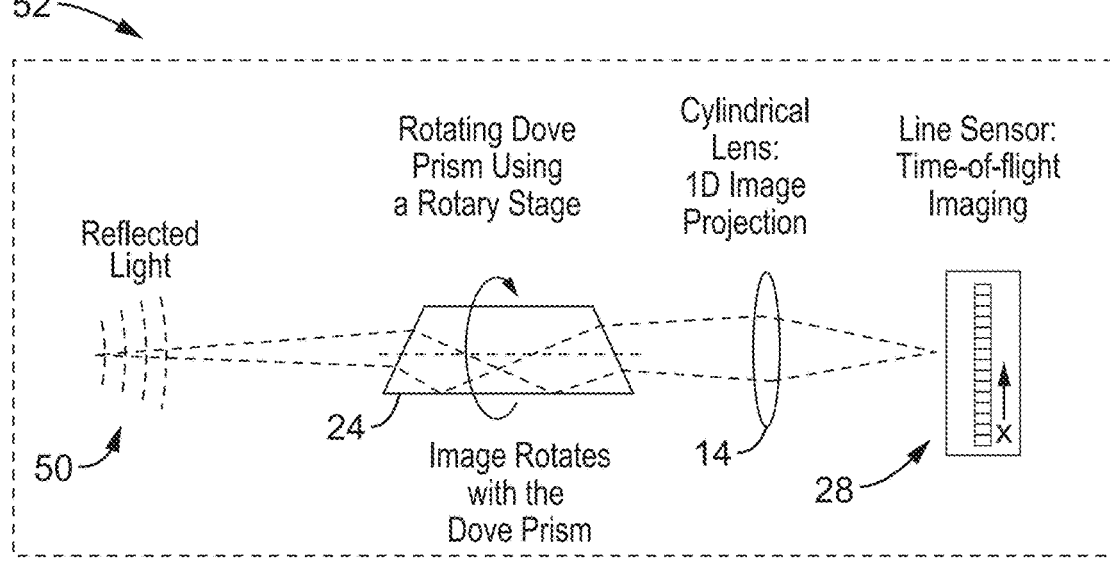
FIG. 7B is a schematic side view of the LIFT camera configuration including either a single dove prism or alternatively an array of dove prisms for measurements of time-of-flight signals of the reflected light by LIFT in the LIDAR application of FIG. 7A.
Figure 7B:
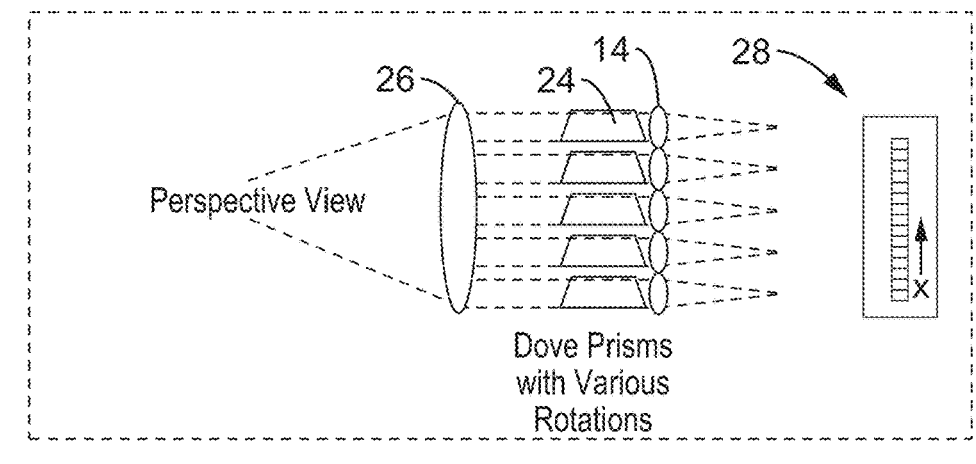

With this structural and computational framework, ultrafast light field tomography can be adapted to several different imaging modalities such as Light Detection and Ranging (Lidar) imaging and hyperspectral imaging. Because LIFT is a passive imaging method, it allows the combination with a pulsed laser illumination to enable snapshot Lidar imaging. In the embodiment shown schematically in FIG. 7A and FIG. 7B, a system with a collimated picosecond laser 42 with a concave lens and a diffuser to create flood illumination 46 on a target surface 48. A LIFT camera 44 is configured to receive reflected light 50 from the target 48. The time-of-flight signals of the reflected light 50 are then measured by a LIFT camera 44 implemented with dove prisms as shown in FIG. 7B. As seen in FIG. 7B, the LIFT camera can be configured 52 with one rotating dove prism 24 and a cylindrical lens 14 for a 1D image projection to a line sensor. Alternatively, the LIFT camera can be configured 54 with a lens 26 and an array of dove prisms 24 and lenslets 14 to line sensor 28 to receive reflections 50 for time-of-flight signal measurement and 3D imaging of the reflected light 50.

Figure 8:
FIG. 8 is a schematic side view of configured for performing Hyperspectral LIFT according to one embodiment of the technology.
Figure 8:
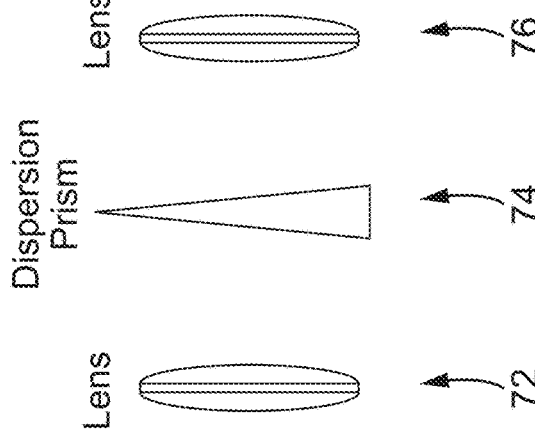
Figure 8:
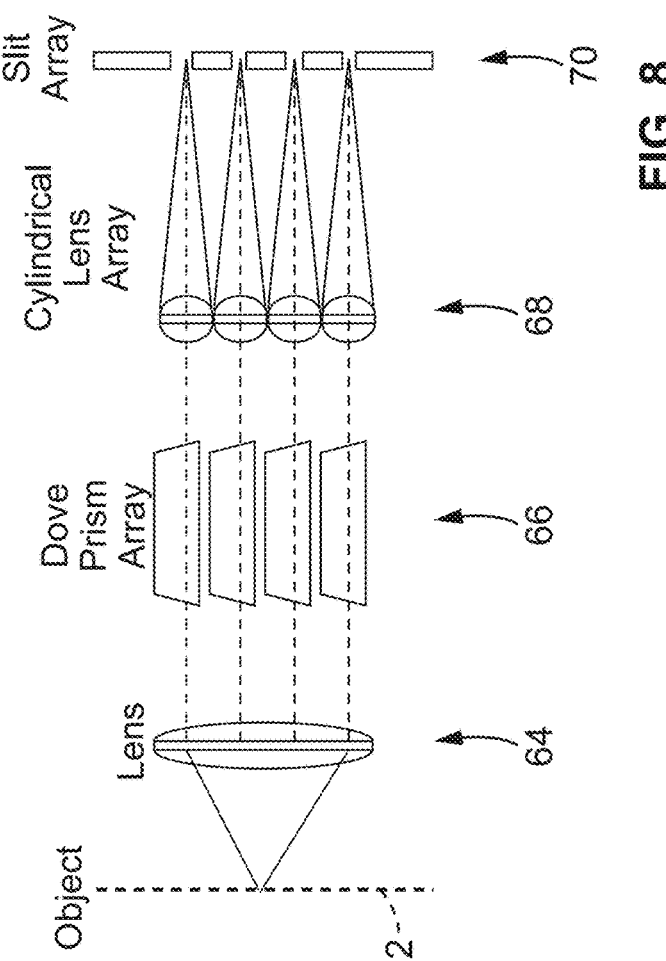

The functionality of LIFT can be expanded to hyperspectral imaging as shown in the implementation of FIG. 8. In this embodiment, the objective 62 is first imaged by a lens 64. At the back pupil plane of the lens 64, an array of dove prisms 66 rotated at various angles is positioned, followed by an array of cylindrical lenses 68. The combination of the dove prisms 66 and cylindrical lenses 68 rotates each image and focuses the resultant image into lines. Next, an array of slits 70 is placed at the focal plane of the cylindrical lenses 68 in order to sample the transformed images. The resulting slit images are dispersed using a combination of the first lens 72, a prism (or a diffractive grating) 74 and a second lens 76. The final dispersed slit images are measured by a 2D detector array 78 such as a CCD or CMOS camera.

To reconstruct the spectral image at a given wavelength, the corresponding projection line images at varied angles are extracted and used to construct the sinogram. The 2D spectral image can then be computed through standard CT reconstruction. Additionally, because the projection images are acquired at various angles, the depth can be derived based on the disparity among different view images. The numerical refocusing, extended depth of field, and 3D rendering can be enabled by standard light field image processing.

Non-line-of sight (NLOS) imaging is an important technique that enables ultrafast (picosecond exposure) cameras to visualize objects that are hidden from direct view. However, widespread implementation of NLOS is limited by the requirement of a high-resolution, two-dimensional ultrafast camera that can process a long sequence of time-resolved data. Current NLOS-enabled cameras must perform scanning in spatial and/or temporal dimensions, lengthening the acquisition time to seconds and restricting the imaging to static or slow-moving objects. Therefore, an ultrafast camera capable of imaging objects that are both rapidly moving and out of the field of focus is provided to realize the full utility of NLOS. The LIFT camera system and methods enable video-quality, NLOS imaging by capturing the complete four-dimensional space (x, y, z, and time) in a single snapshot with exceptional resolution even when objects were in rapid motion or hidden from direct view.

Accordingly, LIFT provides an imaging strategy that can readily exploit a compact 1D sensor like a 1D array of SPAD detectors for high quality NLOS imaging at a 30 Hz video rate by using only a few rotations while offering unique light field capabilities, for example. SPAD detectors feature three prominent advantages: a lower cost, a compact form factor, and a single-photon sensitivity. While 2D SPAD cameras suffer from low fill factors, 1D SPAD detectors can easily accommodate on-chip photon counters on the side of the active pixel and reach a fill factor close to 100%, allowing more efficient light collection. LIFT also opens up the possibility to build 2D camera arrays with 1D sensors for ultrafast or synthetic-aperture imaging, featuring orders of magnitude smaller data load than conventional approaches. The larger baseline and etendue in camera arrays will also enable vastly larger light throughput, making it possible to see through occlusions.

The technology described herein may be better understood with reference to the accompanying examples, which are intended for purposes of illustration only and should not be construed as in any sense limiting the scope of the technology described herein as defined in the claims appended hereto.

Example 1

To demonstrate the fundamental functions of the LIFT system, the apparatus diagramed in FIG. 1 was constructed and tested. Initially, a forward model of the projection data acquisition was devised and the resolution, field of view and noise robustness of the image reconstruction were evaluated. The forward model of the projection data acquisition was derived as $b(\theta)=TR^{\theta}g$, in which g is the vectorized object image, $R^{\theta}$ is the rotation operator, and T denotes the integration along the column direction of the image. The integration operator T can model the non-uniform intensity of the line shaped PSF, a vignetting effect of the lenslet, which is small in the photographic imaging of LIFT By stacking the projection data at different angles, the forward model for LIFT with n lenslets can be completed as:

$$b = \begin{bmatrix} f(\theta_1) \\ \vdots \\ f(\theta_n) \end{bmatrix} = T \begin{bmatrix} R^{\theta 1} \\ \vdots \\ R^{\theta n} \end{bmatrix} g = Ag \qquad (14)$$

Here, A is the linear operator representing the system forward model.

Because the number of projections n is generally smaller than the pixel resolution of the unknown image N, the system forward model is under-determined and hence represents a sparse view CT problem. Therefore, the image was reconstructed by solving the following optimization problem:

$$\text{argmin}\|b - Ag\|_2^2 + \mu\|\varphi(g)\|_1, \qquad (15)$$

where $\varphi(g)$ is a transform function sparsifying the image and $\|\cdot\|_1$ is the $l_1$ norm. The $\mu$ is a hyperparameter that controls the balance between the data fidelity and regularization term. Various transform functions, like total variation, wavelet transform, and discrete cosine transform, can be used to make the image representation sparse. The value $\varphi(g)=g$ was chosen due to its simplicity and suitability for a massively parallel solution.

This equation was solved using the FISTA algorithm on a GPU for optimal speeds. It was found that this LIFT reconstruction was relatively insensitive to the regularization parameter $\mu$: after normalizing the measurement y, setting $\mu$ to 0.05 to about 0.5 leads to good results for all the experiments. For NLOS imaging, in particular, $\mu$ can span a large range (0.01 to about 0.5) without significant influence on the reconstruction quality.

With n projections in LIFT, the complexity for reconstructing a datacube of size (N, N, $N_t$) using m iterations is $O(mnN^2N_t)$. Each iteration includes a gradient step and a simpler l1 regularization step. The gradient step involves one pass of the forward operator A and its adjoint $A^T$, both of which have a complexity of $O(nN^2N_t)$: projection at each angle has a complexity of $O(N^2)$, and the $N_t$ instantaneous images are independently processed at n projection angles. The regularization step has $O(N^2N_t)$ soft shrinkage operations, which is negligible in comparison. Similarly, with a depth resolution of $N_d$, the reconstruction complexity for a 3D scene (x, y, z) is $O(mnN^2N_d)$: each depth is reconstructed independently after shearing the measurement data.

Generally, the image sparsity (percentage of dominant coefficients in the basis) must be proportional to the inverse of the compression factor (N/n: Nyquist sampling rate dividing the system sampling rate) in order to achieve a high-fidelity reconstruction. Therefore, it may be important to analyze the sparsity characteristic of the scene to be captured and choose the number of lenslets wisely to strike a balance between the image quality and resolution. With a compression factor of 18 in this example, LIFT was shown to recover the low frequency structure of cluttered images but not the high frequency details very well.

The resolution and field of view were then evaluated. The effective pixel resolution of LIFT was determined by the 1D sensor pixel number and the number of lenslets. Given n lenslets and a 1D sensor with $N_x$ pixels, the effective imaging resolution for LIFT is $N=N_x \cos \theta_{max}/n$, where $\theta_{max}$ is the maximum projection angle with respect to the normal of 1D sensor, and the term $\cos \theta_{max}$ is there to account for the resampling process.

There was therefore a trade-off between the pixel resolution and image quality. The image resolution can be increased by employing fewer lenslets at the expense of reduced image quality, as the available number of projections is proportionally reduced. With seven lenslets along the streak camera's slit, the effective resolution of current LIFT camera was 128×128.

Despite the trade-off between the pixel resolution and image quality, LIFT represents a highly efficient method for light field acquisition. Using n projections of N pixels for reconstructing an N×N image, LIFT acquires implicitly an n×N×N light field data (n angular resolution and N×N spatial resolution) with only n×N pixels, which is N times less than those of conventional (focus or unfocused) light field cameras, regardless of whether the lenslet number n satisfies the Nyquist sampling criterion or not. Given LIFT's spatial resolution, this fact translates to two orders of magnitude more efficient utilization of the camera pixels.

The field of view of LIFT was reduced by a factor of n, as the 1D sensor was divided to record the object's projection data at different angles. However, there is no inherent limit on the achievable field of view for LIFT since it is straightforward to tailor the relay systems to obtain a desired FOV for target applications.

Example 2

To further demonstrate the capabilities of the system and methods, the image quality of the LIFT system was evaluated. The image quality of LIFT depends on both the compression factor (the number of projections) and the signal to noise ratio of the measurement data. The sampling analysis results indicate that a larger number of projections will fill the k-space more densely and therefore lead to better reconstruction quality in LIFT due to the reduced compression factor.

To evaluate the influence of compression factor, LIFT images for a Shepp-Logan phantom and a cluttered cameraman photograph using different numbers of projections at a resolution of 128×128 were reconstructed and evaluated. The sampling angular range is [0°, 180° ] and the transform function $\varphi(g)$ were chosen as total variation (TV) to encourage sparsity in image gradient. The compression factor varied from ~18 to 1 (Nyquist rate) when the projection number changed from 7 to 128. The PSNR of the reconstructed images versus the compression factor for the phantom and camera-man photograph were also evaluated.

Sampled at the Nyquist rate, the images recovered with a projection number of 128 served as the ground truth reference for calculating the peak signal to noise ratio (PSNR) of other reconstructed images. It is noted that, as the compression factor gets larger (i.e., fewer projections), the PSNR of the reconstructed images becomes smaller and fine image details gradually get washed out. Moreover, the cluttered camera-man photograph renders a smaller PSNR than that of the Shepp-Logan phantom when employing the same compression factor. Therefore, the number of projections must be appropriately scaled to accommodate scenes of different complexity. This is expected and conforms to the general observations in sparse view CT reconstruction.

Since ultrafast imaging with picoseconds resolution is usually shot-noise limited, the noise robustness of LIFT was studied by varying the average number of photons (K) in the recorded projection data. The images were then reconstructed using 7 projections spanning an angular range of [0°, 180° ] by the FISTA algorithm. For comparison, the ground truth images were also simulated using the same average number of photons Kin the image.

The reconstructed and ground truth images of the Shepp-Logan phantom when the average number of photons varied from 4 to 256 were also evaluated. With a few photons, fine details are generally masked out even in the ground truth images, and only a rough structure of the image could be recovered by LIFT. However, with the photon count reaching over 100, the recovered image in LIFT begins to converge to the ideal reconstruction results.

Both data fidelity and regularization terms in the optimization-based formulation were shown to contribute to the improved noise robustness for LIFT reconstruction over filtered backprojection. The data fidelity is a least square term that tends to suppress noises at the expense of resolution. The regularization term is critical for noise attenuation as it denoises intermediate reconstructions in each iteration, which is particularly evident under the framework of regularization by denoising (RED) for inverse problems.

The robustness of the system to noise was also evaluated with a bookshelf scene that suffered from strong interreflections. The globally maximum photon count in the data cube was also varied. For LIFT, the maximum photon counts are in the projection measurement rather than the reconstructed (x, y, t) datacube.

While the point-scanning method recovered the bookshelf with a maximum photon count of 10, LIFT using 21 projections needed 100 counts to recover the main shapes of the bookshelf. This indicated that LIFT using 21 projections is about 10 times nosier than the point-scanning method. Less projections in LIFT requires more photons to recover the hidden scene and tends to produce smoother results. This is expected as less projections will produce stronger reconstruction artefacts and noises.

However, LIFT can readily compensate for its noisier reconstruction by allowing longer exposure time while still maintaining 30 Hz video rate. With 7 projections in a 1D SPAD camera, LIFT can acquire 21 projections using only three rotations, leading to an exposure time of 10 ms at each rotation for imaging at 30 Hz. In contrast, point scanning at 32×32 resolution is still approximately ten times away from 30 Hz, even using an exposure time as short as about 250 μs.

Scanning a 1D SPAD array along one spatial axis can reach 30 Hz at a resolution of 100×100 but only at an exposure time of 300 μs (30 ms/100) for each line, which is 30 times shorter than that of LIFT. Compared with 2D SPAD cameras, LIFT using 1D SPAD array benefits from about 10 times larger fill factor, which is currently around 10% in state-of-the-art 2D designs. Therefore, LIFT can collect over ten times more photons to compensate for its higher noise level while offering unique advantages: compressive data acquisition and full-fledged light field capabilities. Given an (x, y, t) datacube of 128×128×1000, acquired with 8-bit precision, the resultant data load is 16 Megabytes, more than twice of that in 4K ultra high-definition camera. Streaming such data at 30 Hz reliably requires the use of nontrivial compression algorithms. Instead, LIFT with 21 projections reduced the data load during acquisition more than six times. Moreover, the light field capability of LIFT is inherently challenging to implement in scanning-based methods or 2D SPAD cameras without incurring a substantial increase in system complexity and data load.

Example 3

In order to demonstrate the LIFT system in ultrafast imaging, a light-in-flight scene was captured that is beyond the capability of existing ultrafast cameras. A light-diffusing fiber with internal nanostructures that scatter out a small fraction of light from its core was wrapped into a helical shape with a depth range stretching over 80 mm was imaged. After coupling a picosecond pulsed laser into the fiber, the internal laser pulse evolution was recorded at 0.5 T frames per second with a native temporal resolution of about 3 ps.

It is challenging for cameras with a fixed focus to resolve the helical fiber very well when spanning a large depth range. Images of the fiber were obtained at different focal settings, emulated by computationally refocusing the LIFT camera at different depths and integrating time-resolved images along the temporal axis. For each preset focal depth, only part of the helical fiber remained sharp and ghost images begin to emerge for heavily defocused parts.

By comparison, LIFT could synthesize an all-in-focus image to resolve the entire helical fiber structure by leveraging its post-capture refocusing capability as illustrated in FIG. 3. With seven angular components, the LIFT process effectively increased the depth of field by seven-fold, which was notably achieved without compromising light throughput. Moreover, LIFT enabled the extraction of the scene depth at each time instant via the depth-from-focus method, thereby revealing the complete 4D spatiotemporal dimensions of the event under observation.

In this example, the depth retrieval accuracy without the relay system was $d^2 \Delta L/(D\alpha) \approx 2$ mm, with d and a being the distance from the lenslet array to the object and 1D sensor, respectively. The lenslet array baseline D and the pixel size $\Delta L$ serve similar roles as those in stereo methods: a large baseline and a smaller pixel yield a better depth resolution.

After depth extraction and extending the depth of field, the 3D imaging of laser pulse propagation inside the helical fiber occurred at several representative time instants that were recorded. The retrieved 3D structure of the fiber, obtained by integrating all frames, agreed qualitatively well with the photograph, validating LIFT's capacity in visualizing extended 3D objects. Such extended depth of field and 3D imaging capabilities are defining features of LIFT over other 2D ultrafast cameras.

The deep adjoint neural network accelerated the reconstruction and improved the image quality by learning and mitigating the system's implementation limitations. Specifically, DANN (or similar machine learning technique) can alleviate the limited view problem, which refers to a degraded tomographic image reconstruction when the projection data does not span the complete angular range of [0°, 180° ].

A frequency cone along the $k_y$ direction in the k-space may not be sampled by the LIFT camera. This was manifested in the all-in-focus images of the helical fiber in the horizontal features on the top and bottom parts show an inferior resolution and consequently appeared dimmer. However, by training the DANN with a dataset containing similar challenging cases, the network could efficiently learn and mitigate this problem.

To further demonstrate the approach, the cylindrical lenslet arrangement for an automatically extended depth of field was arranged as shown in FIG. 4A and trained the DANN network for the system using an image set collected from MNIST and FashionMNIST dataset. The training set was created so that approximately 60% of its images contain rich spatial frequencies inside the missing cone of the system to enable efficient learning of reconstruction under limited view constraints. The test dataset was composed primarily of images showing strong features along the horizontal direction to illustrate the pessimistic recovery performance for the scenes afflicted by the limited view problem. While iterative results tend to blur horizontal features as in the helical fiber, the DANN network clearly recovered the images with most horizontal features that were well delineated.

The laser pulse propagation inside the helical fiber was re-captured using the automatically extended depth-of-field version of LIFT but re-wrapped to emphasize its horizontal features for an escalated limited view problem. The recovered images at representative time instants by iterative methods and DANN were compared. As the laser pulse propagated to the horizontal parts of the fiber, iterative results were seen to get dimmer whereas the DANN procedure manages to recover the signal decently. The lack of signals in the iterative reconstruction is more evident in the time-integrated images. Notably, the helical fiber (spanning a ~80 mm depth range) is well resolved here without the need of computational refocusing, corroborating the automatically extended depth of field.

Currently, the iterative method takes about 2.5 seconds to reconstruct a (128, 128, 1000) datacube when implemented on an RTX2080Ti graphical processing unit (GPU). By contrast, DANN implemented on the same GPU using PyTorch costs only about 0.5 seconds after training (~1.5 hour), a five times speedup. The reconstruction speed can be further accelerated by efficient scaling of the neural network and exploiting more powerful GPUs or alternative hardware like field programmable gate arrays for network implementation.

Example 4

The LIFT system with non-line-of-sight imaging were demonstrated with a picosecond laser (532 nm light at 100 Hz with 6 ps pulse width and 2 mW average power) that was collimated onto a diffusing wall made of a white foam plate. The LIFT camera was focused on the wall with a field of view of 600 mm×800 mm. The laser position was fixed around the center of the field of view (FOV). Ambient room light was turned on during the experiments. The geometric configuration of the system was measured by a structured-light depth camera. The 3D position of the wall (a dense point cloud), the laser incident spot and the LIFT camera were all obtained in the coordinate system of the depth camera. To relate each pixel of the LIFT camera to the imaged spot on the wall, a grid pattern was projected on the flat wall and imaged by both the LIFT and depth cameras. The two images were registered by a homography matrix, by which a pixel-to-pixel correspondence was established between the LIFT camera and the depth camera. Each pixel's 3D position on the wall was then identified for LIFT camera by indexing the wall's point cloud using the correspondence map.

After reconstructing the 2D time-resolved data, the data was unwarped using the calibrated geometric configuration and then reconstructed the hidden scene with the phasor-field method. To improve noise robustness of LIFT for NLOS imaging, the weighting factors were extended to the phasor-field method. Under the phasor-field framework, the signals $y_r(r_p, t)$ are convolved with a bandpass-filtering kernel h(t) before backprojection reconstruction (the imaginary part is omitted here as it is similarly processed):

$$I(r_v, t) = \int_{-w}^{w} y_r(r_p, t) * h(t - \tau) dr_p \tag{16}$$

where $r_p$ and $r_v$ index the detection point on the wall and the reconstruction voxel, respectively.

$$\tau = \frac{r_s + r_p - 2r_v}{c}$$

is the round-trip travel time from the illumination point $r_s$ to the voxel $r_v$ and back to the detection point. The coherence factor is extended here on the filtered signals:

$$CF(r_v) = \frac{1}{K} \sum_{i=1}^{K} \frac{I(r_v, t = \tau + i\Delta t)}{I_q(r_v, t)} \tag{17}$$

$$I_q(r_v, t) = \int_{-w}^{w} \{y_r(r_p, t) * h(t - \tau)\}^2 dr_p, \tag{18}$$

where K is the temporal kernel size, and $\Delta t$ is the time bin width. It evaluates the spatial coherence of the signals across the sampling grid: backscattered signals from the hidden objects are spatially correlated on the wall, whereas noises tend to be independent of each other. The reconstruction volume weighted by the coherence factor is then:

$$I(r_v)=I(r_v,t=0)CF(r_v). \tag{19}$$

The noises were attributed to the measurement shot-noises, ambient light, inter-reflections and LIFT reconstruction artefacts. The ambient light was generally stable during the exposure time and can be modelled by a slowly varying function of time. Similarly, the inter-reflections $r(r_p,t)$ tends to show as low frequency components in $y_r(r_p, t)$. Therefore, a properly chosen h(t) will effectively attenuate both of them. Their primary effects are on the measurement shot-noises at each time bin, which are determined by the total photon count from all origins.

NLOS reconstruction using the phasor-field method had a complexity of $O(N^5)$ or $O(N^3 \log N)$ when implemented with elliptical backprojection or fast Rayleigh-Sommerfeld diffraction. To accelerate computation, the phasor-field reconstruction was implemented on a GPU (Nvidia RTX2080Ti) using CUDA. For 3D rendering, the volumetric image was normalized and soft-thresholded to improve visibility. For a 128×128×128 volume, the phasor-field reconstruction time was approximately 2.5 seconds. Combined with the LIFT reconstruction time of 2.5 seconds using iterative methods (0.5 s using DANN) at a resolution of 128×128×1016, the total time of NLOS imaging was about 5.0 (or 3.0) seconds.

Mediated by a relay wall, NLOS imaging shows drastically different characteristics from natural photograph in that the instantaneous (and steady state) images on the wall are generally smooth and highly compressible, even for complex hidden scenes. To simulate the recoverable (x, y, t)datacube by the LIFT camera, a two-step process was employed: 1) changing the PSF of the camera in the synthetic dataset to line-shaped PSFs to model the LIFT camera, and 2) reconstructing the datacube by the iterative FISTA algorithm that was used due to its greater flexibility to handle LIFT models using different numbers of projections. As NLOS imaging typically employs compact SPAD sensors and a recording of the complete (x, y, t)datacube with a single laser shot is not required, the LIFT camera model A was synthesized to encompass up to tens of projections that sample uniformly the complete angular range of [0°, 180°]. This was easily achieved by a few rotations of a 1D SPAD based LIFT camera. The hidden scenes were reconstructed at a volumetric resolution of 128×128×128 using the extended phasor-field method.

It was shown that LIFT can recover both the instantaneous images and the hidden scene using only 14 projections, corresponding to approximately 10% of the data load in the point-scanning method. Compared with the ground truth images, LIFT results tend to be smoother, particularly for the cases using a small number of projections. This is attributed to the LIFT's radial sampling pattern in k-space: high spatial frequencies are more sparsely sampled. Nonetheless, LIFT using 7 to 14 projections can still detect, though not resolve, the smallest strips in the resolution target. The reconstruction by LIFT using 7 projections rendered the main shapes of the resolution target despite of some artefacts.

Example 5

Being able to acquire a large-scale 4D data cube (x, y, u(or z), t) with a single snapshot makes it possible for NLOS imaging at a 30 Hz video rate with LIFT, which is critical for applications like navigation and surveillance. To demonstrate LIFT for NLOS imaging, the camera was focused on a diffusing wall with an FOV about 600 mm×800 mm. A picosecond pulsed laser was collimated onto the wall, and the incident spot was blocked by a tiny stop at the intermediate image plane of the relay lens to avoid the directly backscattered light from the wall. The signals from the hidden scene were recorded by LIFT with a single laser shot. With an average power at 2 mW, multiple laser shots were averaged for imaging large static scenes (total acquisition time being 0.2 s using 20 shots for objects placed about 0.3 m from the wall and one second using 100 shots for objects placed >1 m from the wall). The hidden scene was then reconstructed using the extended phasor-field method. Both the shapes and 3D locations of the scenes were well reconstructed in the current LIFT system with the use of only seven projections. The light field capabilities of LIFT can also substantially lessen the focusing requirement for image acquisition, allowing non-planar walls to be exploited for NLOS imaging.

Although NLOS reconstruction using the phasor-field does not impose any restrictions on the geometry of the relay wall, light collection is confined to the lens system's depth of field for unambiguous separation of signals on the wall.

As a result, most NLOS implementations employed a flat or slightly curved wall. Although a depth camera has the luxury of a tiny aperture (thus large depth of field) to calibrate the imaging geometry, the resultant quadratic reduction of light collection prevents similarly small apertures being used in a NLOS camera. This makes it challenging to accommodate the entire wall within NLOS camera's depth of field in real-world applications. LIFT's automatically extended depth of field can potentially lift this restriction without any computational refocusing burden, paving the way to efficient light collection over curved or even disconnected surfaces.

To showcase video-rate NLOS imaging, a hidden scene consisting of a static strip and one circular plate was configured, which was mounted on a rail track (~0.3 m from the wall) and manually translated back-and-forth by about 150 mm within three seconds across the wall (the moving speed being ~120 mm/s or ~15% of the wall per second). LIFT recorded the 2D time-resolved data with an exposure time of 10 ns at a repetition rate of 100 Hz, and three frames were averaged to improve the SNR, yielding a frame rate of ~30 Hz. LIFT captured the motion of the circular plate faithfully as compared with the reference camera. In contrast to the previous NLOS tracking that uses a limited number of virtual sensor points for localizing individual objects at a few frames per second, LIFT achieved a full 3D imaging of the hidden scene at 30 Hz.

The snapshot acquisition enabled LIFT to achieve drastically faster NLOS imaging with a resolution and quality close to those in dense point-scanning methods, allowing a low laser power to be used for imaging over 1 m scale. By scaling according to the $r^4$ photon decay law in NLOS imaging, LIFT is expected to reach an imaging volume around 3 m×3 m×3 m with an average laser power of 160 mW.

From the description herein, it will be appreciated that the present disclosure encompasses multiple implementations which include, but are not limited to, the following:

A light field tomography (LIFT) apparatus, comprising: (a) a cylindrical lens with an invariant axis, the lens configured to produce parallel beam projections of an object in an image plane parallel to the invariant axis of the cylindrical lens; (b) an array cylindrical lensets, each lenslet with an invariant axis oriented at a distinct angle; and (c) an imaging device positioned after the array of lenslets, the device configured to image the parallel beam projections from each lenslet; (d) wherein the lenslets are arranged in a sequence of their invariant axis' angles with respect to the imaging device; and (e) wherein a single snapshot image of the object can be produced from simultaneously acquired beam projections from the sequence of lenslets.

The apparatus of any preceding or following implementation, further comprising: a Dove prism positioned between the cylindrical lens and the array of lenslets.

The apparatus of any preceding or following implementation, further comprising: an array of Dove prisms positioned between the cylindrical lens and the array of lenslets, each Dove prism optically coupled with a lenslet.

The apparatus of any preceding or following implementation, further comprising: a slit array positioned between the cylindrical lenslet array at a focal point of the lenslets and the imaging device; a first imaging lens; a dispersive element; and a second imaging lens; wherein dispersed slit images are measured by the imaging device and produce a hyperspectral image.

The apparatus of any preceding or following implementation, wherein the dispersive element is selected from the group of a dispersion prism and a diffractive grating.

The apparatus of any preceding or following implementation, further comprising: a target illumination light source, wherein reflected light from a target is imaged by the imaging device.

The apparatus of any preceding or following implementation, wherein the target illumination light source comprises a collimated picosecond laser with a concave lens and diffuser to produce pulsed laser illumination of the target.

The apparatus of any preceding or following implementation, further comprising: an array of Dove prisms, each Dove prism optically coupled with a lenslet.

The apparatus of any preceding or following implementation, the imaging device further comprising: a photocathode with an entrance slit and a lens optically coupled to the array of lenslets; and an electronic image sensor selected from the group of a charge-coupled device (CCD) and a (CMOS sensor).

The apparatus of any preceding or following implementation, the imaging device further comprising: a streak camera with an entrance slit and a lens optically coupled to the array of lenslets; and a charge-coupled device (CCD) camera.

The apparatus of any preceding or following implementation, further comprising: (a) a processor configured to control the lenses and imaging device; and (b) a non-transitory memory storing instructions executable by the processor; (c) wherein the instructions, when executed by the processor, perform steps comprising: (i) acquiring a dataset of image data from the imaging device over time; and (ii) reconstructing 2D, 3D or 4D images from the acquired dataset.

The apparatus of any preceding or following implementation, wherein the instructions when executed by the processor further perform steps comprising: applying a trained deep adjoint neural network (DANN) to the reconstruction to accelerate reconstruction and improve image quality; and displaying the reconstructed image on a display.

The apparatus of any preceding or following implementation, wherein the instructions when executed by the processor further perform steps comprising: controlling the depth of field; and forming time-integrated 3D images.

The apparatus of any preceding or following implementation, further comprising: a target illumination light source, wherein reflected light from the target is imaged by the imaging device.

The apparatus of any preceding or following implementation, wherein the instructions when executed by the processor further perform steps comprising: controlling the target illumination light source; and controlling the rate if image data acquisition.

A light field tomography imaging method, comprising: (a) providing a light field tomography apparatus comprising: (i) a cylindrical lens with an invariant axis, the lens configured to produce parallel beam projections of an object in an image plane parallel to the invariant axis of the cylindrical lens; (ii) an array cylindrical lenslets, each lenslet with an invariant axis oriented at a distinct angle; and (iii) an imaging device positioned after the array of lenslets, the device configured to image the parallel beam projections from each lenslet; (b) acquiring parallel beam projections of a target by the imaging device; (c) ordering beam projections (x, e) into sinograms; and (d) reconstructing 2D (x, y) images from the sinograms.

The method of any preceding or following implementation, further comprising: acquiring parallel beam projections of a target by the imaging device; ordering beam projections (x, e) into sinograms; and reconstructing 3D (x, y, t) or 4D (x, y, z, t) images from the sinograms.

The method of any preceding or following implementation, wherein the 3D reconstruction further comprises: refocusing on different depths to produce a focal stack; co-registering the focal stack to correct image shifts; filtering the co-registered focal stack with a denoising algorithm; computing a focus measure for each pixel; and mapping the depth of each pixel to yield a 3D image (x, y, z).

The method of any preceding or following implementation, the light field tomography apparatus further comprising: an array of Dove prisms positioned between the cylindrical lens and the array of lenslets, each Dove prism optically coupled with a lenslet.

The method of any preceding or following implementation, the light field tomography apparatus further comprising: a slit array positioned between the cylindrical lenslet array at a focal point of the lenslets and the imaging device; a first imaging lens; a dispersive element; and a second imaging lens; wherein dispersed slit images are measured by the imaging device and produce a hyperspectral image.

The method of any preceding or following implementation, wherein the imaging device is selected from the group consisting of a charge-coupled device (CCD), a single-photon avalanche diode (SPAD) and a (CMOS sensor).

The method of any preceding or following implementation, the light field tomography apparatus further comprising: a target illumination light source, wherein reflected light from an illuminated target is imaged by the imaging device.

The method of any preceding or following implementation, wherein the target illumination light source comprises a collimated picosecond laser with a concave lens and diffuser to produce pulsed laser illumination of the target.

A light field tomography imaging method, comprising: (a) providing a light field tomography apparatus comprising: (i) an imaging device having an entrance slit and a lens; and (ii) a plurality of cylindrical lensets positioned in an array wherein each lenslet is oriented at a distinct angle; (iii) the lenslet array positioned between the lens and entrance slit and aligned with the entrance slit, wherein the lenslets are arranged in a sequence of their invariant axis' angles with respect to the slit; (b) imaging a 3D target by the imaging device lens to the intermediate image space, from which the cylindrical lenslet array forms differently projected sub-images onto the slit plane; and (c) using a field stop in the intermediate image plane to reduce the field of view to avoid potential sub-image overlap between adjacent lenslets; (d) wherein the imaging device relays 1D projection images extracted by the entrance slit onto a photocathode, converts the images to an electronic domain, and deflects the images onto different rows of a CCD detector according to time of arrival of photons.

The method of any preceding or following implementation, the light field tomography apparatus further comprising: an array of Dove prisms positioned between the cylindrical lens and the array of lenslets, each Dove prism optically coupled with a lenslet.

A method for acquiring an image of an object, the method comprising: providing a cylindrical lens, an array of cylindrical lenslets oriented at distinct angles, and a 1D sensor positioned at the center of the image space; acquiring en-face parallel beam projections of the object using the cylindrical lens; acquiring a parallel beam projection of the image along the invariant axis direction; wherein the cylindrical lens optically transforms point sources in object space into parallel lines in image space; and wherein line direction in the image space is parallel to the invariant axis (the axis without optical power) of the cylindrical lens; decomposing the optical transformation of the object by performing pin-hole image formation; and substituting the point spread function (PSF) into a line parallel with the cylindrical lens' invariant axis; wherein line-shaped PSF enables an individual sensor pixel to integrate image signals along a particular line; wherein projection at different angles can be recorded by rotating the cylindrical lenslet with respect to the 1D sensor; and using the array of cylindrical lenslets oriented at distinct angles to obtain enough beam projections simultaneously to recover the image with a single snapshot.

As used herein, term "implementation" is intended to include, without limitation, embodiments, examples, or other forms of practicing the technology described herein.

As used herein, the singular terms "a," "an," and "the" may include plural referents unless the context clearly dictates otherwise. Reference to an object in the singular is not intended to mean "one and only one" unless explicitly so stated, but rather "one or more."

Phrasing constructs, such as "A, B and/or C", within the present disclosure describe where either A, B, or C can be present, or any combination of items A, B and C. Phrasing constructs indicating, such as "at least one of" followed by listing a group of elements, indicates that at least one of these group elements is present, which includes any possible combination of the listed elements as applicable.

References in this disclosure referring to "an embodiment", "at least one embodiment" or similar embodiment wording indicates that a particular feature, structure, or characteristic described in connection with a described embodiment is included in at least one embodiment of the present disclosure. Thus, these various embodiment phrases are not necessarily all referring to the same embodiment, or to a specific embodiment which differs from all the other embodiments being described. The embodiment phrasing should be construed to mean that the particular features, structures, or characteristics of a given embodiment may be combined in any suitable manner in one or more embodiments of the disclosed apparatus, system, or method.

As used herein, the term "set" refers to a collection of one or more objects. Thus, for example, a set of objects can include a single object or multiple objects.

Relational terms such as first and second, top and bottom, and the like may be used solely to distinguish one entity or action from another entity or action without necessarily requiring or implying any actual such relationship or order between such entities or actions.

The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element.

As used herein, the terms "approximately", "approximate", "substantially", "essentially", and "about", or any other version thereof, are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "coupled" as used herein is defined as connected, although not necessarily directly and not necessarily mechanically. A device or structure that is "configured" in a certain way is configured in at least that way but may also be configured in ways that are not listed.

Benefits, advantages, solutions to problems, and any element(s) that may cause any benefit, advantage, or solution to occur or become more pronounced are not to be construed as a critical, required, or essential features or elements of the technology describes herein or any or all the claims.

In addition, in the foregoing disclosure various features may grouped together in various embodiments for the purpose of streamlining the disclosure. This method of disclosure is not to be interpreted as reflecting an intention that the claimed embodiments require more features than are expressly recited in each claim. Inventive subject matter can lie in less than all features of a single disclosed embodiment.

The abstract of the disclosure is provided to allow the reader to quickly ascertain the nature of the technical disclosure. It is submitted with the understanding that it will not be used to interpret or limit the scope or meaning of the claims.

It will be appreciated that the practice of some jurisdictions may require deletion of one or more portions of the disclosure after that application is filed. Accordingly the reader should consult the application as filed for the original content of the disclosure. Any deletion of content of the disclosure should not be construed as a disclaimer, forfeiture, or dedication to the public of any subject matter of the application as originally filed.

The following claims are hereby incorporated into the disclosure, with each claim standing on its own as a separately claimed subject matter.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A light field tomography (LIFT) apparatus, comprising:
(a) a cylindrical lens with an invariant axis, the lens configured to produce parallel beam projections of an object in an image plane parallel to the invariant axis of the cylindrical lens;
(b) an array of cylindrical lenslets, which is separate from the cylindrical lens, wherein each lenslet of the array of cylindrical lenslets has an invariant axis oriented at a distinct angle, and positioned in line with the cylindrical lens; and
(c) an imaging device positioned after the array of lenslets, with the array of cylindrical lenslets positioned between the cylindrical lens and the imaging device, wherein said imaging device is configured to image said parallel beam projections which pass through each lenslet of the array of cylindrical lenslets into said imaging device;
(d) wherein said lenslets of the array of cylindrical lenslets are arranged in a sequence of their invariant axis' angles with respect to the imaging device;
(e) a Dove prism positioned between the cylindrical lens and the array of lenslets, or an array of Dove prisms positioned between the cylindrical lens and the array of lenslets, each Dove prism optically coupled with a lenslet; and
(f) wherein a single snapshot image of the object is produced by the imaging device from simultaneously acquired beam projections from the sequence of lenslets.

2. The apparatus of claim 1, further comprising:
a slit array positioned between the cylindrical lenslet array at a focal point of the lenslets and the imaging device;
a first imaging lens;
a dispersive element; and
a second imaging lens;
wherein dispersed slit images are measured by the imaging device and produce a hyperspectral image.

3. The apparatus of claim 2, wherein said dispersive element is selected from the group of a dispersion prism and a diffractive grating.

4. The apparatus of claim 1, further comprising:
a target illumination light source, wherein reflected light from a target is imaged by the imaging device.

5. The apparatus of claim 4, wherein said target illumination light source comprises a collimated picosecond laser with a concave lens and diffuser to produce pulsed laser illumination of the target.

6. The apparatus of claim 4, further comprising:
an array of Dove prisms, each Dove prism optically coupled with a lenslet of the array of cylindrical lenslets.

7. The apparatus of claim 1, said imaging device further comprising:

a photocathode with an entrance slit and a lens optically coupled to the array of lenslets; and
an electronic image sensor selected from the group of a charge-coupled device (CCD) and a complementary metal oxide semiconductor (CMOS) sensor.

8. The apparatus of claim 1, said imaging device further comprising:
a streak camera with an entrance slit and a lens optically coupled to the array of lenslets; and
a charge-coupled device (CCD) camera.

9. The apparatus of claim 1, further comprising:
(a) a processor configured to control said lenses and imaging device; and
(b) a non-transitory memory storing instructions executable by the processor;
(c) wherein said instructions, when executed by the processor, perform steps comprising:
(i) acquiring a dataset of image data from the imaging device over time; and
(ii) reconstructing 2D, 3D or 4D images from the acquired dataset.

10. The apparatus of claim 9, wherein said instructions when executed by the processor further perform steps comprising:
applying a trained deep adjoint neural network (DANN) to the reconstruction; and
displaying the reconstructed image on a display.

11. The apparatus of claim 9, wherein said instructions when executed by the processor further perform steps comprising:
controlling the depth of field; and
forming time-integrated 3D images.

12. The apparatus of claim 9, further comprising:
a target illumination light source, wherein reflected light from the target is imaged by the imaging device.

13. The apparatus of claim 12, wherein said instructions when executed by the processor further perform steps comprising:
controlling the target illumination light source; and
controlling a rate of image data acquisition.

14. A light field tomography imaging method, comprising:
(a) providing a light field tomography apparatus comprising:
(i) a cylindrical lens with an invariant axis, the lens configured to produce parallel beam projections of an object in an image plane parallel to the invariant axis of the cylindrical lens;
(ii) an array of cylindrical lenslets, each lenslet with an invariant axis oriented at a distinct angle; and
(iii) an array of Dove prisms positioned between the cylindrical lens and the array of lenslets, each Dove prism optically coupled with a lenslet of the array of cylindrical lenslets;
(iv) an imaging device positioned after the array of lenslets, said device configured to image said parallel beam projections from each lenslet;
(b) acquiring parallel beam projections of a target by the imaging device;
(c) ordering the acquired beam projections having spatial axis and distinct angles $(x, \theta)$ into sinograms; and
(d) reconstructing 2D $(x, y)$ images from the sinograms.

15. The method of claim 14, further comprising:
reconstructing 3D $(x, y, t)$ or 4D $(x, y, z, t)$ images from the sinograms.

16. The method of claim 15, wherein said 3D reconstruction further comprises:

US 12,631,895 B2

29 refocusing on different depths to produce a focal stack;
co-registering the focal stack to correct image shifts;
filtering the co-registered focal stack with a denoising
algorithm;
computing a focus measure for each pixel; and
mapping the depth of each pixel to yield a 3D image (x,
y, z).

17. The method of claim 14, said light field tomography
apparatus further comprising:
a slit array positioned between the cylindrical lenslet array
at a focal point of the lenslets and the imaging device;
a first imaging lens;
a dispersive element; and
a second imaging lens;
wherein dispersed slit images are measured by the imag-
ing device and produce a hyperspectral image.

18. The method of claim 14, wherein said imaging device
is selected from the group consisting of a charge-coupled
device (CCD), a single-photon avalanche diode (SPAD) and
a complementary metal-oxide semiconductor (CMOS) sen-
sor.

19. The method of claim 14, said light field tomography
apparatus further comprising:
a target illumination light source, wherein reflected light
from an illuminated target is imaged by the imaging
device.

20. The method of claim 19, wherein said target illumi-
nation light source comprises a collimated picosecond laser
with a concave lens and diffuser to produce pulsed laser
illumination of the target.

21. A light field tomography imaging method, compris-
ing:
(a) providing a light field tomography apparatus compris-
ing:
(i) an imaging device having an entrance slit and a lens;
and
(ii) a plurality of cylindrical lenslets positioned in a
cylindrical lenslet array wherein each lenslet is ori-
ented at a distinct angle;
(iii) the cylindrical lenslet array positioned between the
lens and entrance slit and aligned with the entrance
slit, wherein the lenslets are arranged in a sequence
of their invariant axis' angles with respect to the
entrance slit;
(b) imaging a 3D target by the imaging device lens to an
intermediate image space, from which the cylindrical
lenslet array forms differently projected sub-images
onto a plane of the entrance slit; and
(c) using a field stop in the intermediate image plane to
reduce a field of view to avoid potential sub-image
overlap between adjacent lenslets;
(d) wherein the imaging device relays 1D projection
images extracted by the entrance slit onto a photocath-
ode, converting images to an electronic domain, and
deflects the images onto different rows of a charge-
coupled device (CCD) detector according to time of
arrival of photons.

22. The method of claim 21, said light field tomography
apparatus further comprising:
an array of Dove prisms positioned between the cylindri-
cal lens and the array of lenslets, each Dove prism
optically coupled with a lenslet.

23. A light field tomography (LIFT) apparatus, compris-
ing:

30

(a) a cylindrical lens with an invariant axis, the lens
configured to produce parallel beam projections of an
object in an image plane parallel to the invariant axis of
the cylindrical lens;
(b) an array of cylindrical lenslets, which is separate from
the cylindrical lens, wherein each lenslet of the array of
cylindrical lenslets has an invariant axis oriented at a
distinct angle, and positioned in line with the cylindri-
cal lens; and
(c) an imaging device positioned after the array of lens-
lets, with the array of cylindrical lenslets positioned
between the cylindrical lens and the imaging device,
wherein said imaging device is configured to image
said parallel beam projections which pass through each
lenslet of the array of cylindrical lenslets into said
imaging device;
(d) wherein said lenslets of the array of cylindrical
lenslets are arranged in a sequence of their invariant
axis' angles with respect to the imaging device;
(e) an array of Dove prisms, each Dove prism optically
coupled with a lenslet of the array of cylindrical
lenslets;
(f) a target illumination light source, wherein reflected
light from a target is imaged by the imaging device; and
(g) wherein a single snapshot image of the object is
produced by the imaging device from simultaneously
acquired beam projections from the sequence of lens-
lets.

24. A light field tomography (LIFT) apparatus, compris-
ing:
(a) a cylindrical lens with an invariant axis, the lens
configured to produce parallel beam projections of an
object in an image plane parallel to the invariant axis of
the cylindrical lens;
(b) an array of cylindrical lenslets, which is separate from
the cylindrical lens, wherein each lenslet of the array of
cylindrical lenslets has an invariant axis oriented at a
distinct angle, and positioned in line with the cylindri-
cal lens; and
(c) an imaging device positioned after the array of lens-
lets, with the array of cylindrical lenslets positioned
between the cylindrical lens and the imaging device,
wherein said imaging device is configured to image
said parallel beam projections which pass through each
lenslet of the array of cylindrical lenslets into said
imaging device;
(d) wherein said lenslets of the array of cylindrical
lenslets are arranged in a sequence of their invariant
axis' angles with respect to the imaging device;
(e) a processor configured to control said lenses and
imaging device; and
(f) a non-transitory memory storing instructions execut-
able by the processor;
(g) wherein said instructions, when executed by the
processor, perform steps comprising:
(i) acquiring a dataset of image data from the imaging
device over time;
(ii) reconstructing 2D, 3D or 4D images from the
acquired dataset;
(iii) applying a trained deep adjoint neural network
(DANN) to the reconstruction; and
(iv) displaying the reconstructed image on a display.

* * * * *